US007071384B2

(12) United States Patent
Howard et al.

(10) Patent No.: US 7,071,384 B2
(45) Date of Patent: Jul. 4, 2006

(54) METHODS FOR COMMERCIAL PRODUCTION OF HETEROLOGOUS LACCASE IN PLANT TISSUE AND EXTRACTION OF THE LACCASE FROM PLANT SEED

(75) Inventors: John A. Howard, College Station, TX (US); Elizabeth E. Hood, Jonesboro, AR (US); Michele Bailey Piatchek, Maryland Heights, MD (US)

(73) Assignee: Genencor International, Inc., Palo Alto, CA (US)

( * ) Notice: Subject to any disclaimer, the term of this patent is extended or adjusted under 35 U.S.C. 154(b) by 547 days.

(21) Appl. No.: 10/164,775

(22) Filed: Jun. 6, 2002

(65) Prior Publication Data

US 2003/0110537 A1     Jun. 12, 2003

Related U.S. Application Data

(63) Continuation-in-part of application No. 09/403,686, filed as application No. PCT/US97/04526 on Mar. 20, 1997, now Pat. No. 6,504,085.

(60) Provisional application No. 60/040,119, filed on Mar. 7, 1997.

(51) Int. Cl.
*C12N 15/82* (2006.01)

(52) U.S. Cl. ...................................... 800/298; 800/278
(58) Field of Classification Search ................ 800/278, 800/298; 530/412
See application file for complete search history.

(56) References Cited

U.S. PATENT DOCUMENTS

| 5,420,034 A | 5/1995 | Kridl et al. |
| 5,480,801 A | 1/1996 | Wahleithner et al. |
| 5,618,482 A | 4/1997 | Olesen et al. |
| 5,667,531 A | 9/1997 | Yaver et al. |
| 5,693,506 A | 12/1997 | Rodriquez |
| 5,767,379 A | 6/1998 | Baszczynski et al. ....... 800/205 |
| 5,770,418 A | 6/1998 | Yaver et al. |
| 5,804,694 A | 9/1998 | Bruce et al. ................ 800/205 |
| 5,889,189 A | 3/1999 | Rodriguez et al. ........ 800/205 I |
| 6,252,134 B1 | 6/2001 | Vasil et al. .................. 800/278 |

FOREIGN PATENT DOCUMENTS

| EP | 0255378 A | 8/1988 |
| WO | 9400992 A | 1/1994 |
| WO | 9640949 A | 12/1996 |
| WO | 9709431 | 3/1997 |
| WO | 9710347 A | 3/1997 |
| WO | 9717453 A | 3/1997 |
| WO | 9745549 | 12/1997 |
| WO | 9811205 | 8/1998 |
| WO | WO 00/20615 | * 4/2000 |
| WO | 0005381 | 5/2000 |

OTHER PUBLICATIONS

Hood et al, 2003, Plant Biotechnol. J. 1:129-140.*
Fiedler, U. and Conrad, U. "High-Level production and Long-Term Storage of Engineered Antibodies in Transgenic Tobacco Seeds." 1995, Bio/Technology, vol. 13, pp. 1090-1093.
Baumlein, H. et al., "Upstream sequences regulating legumin gene expression in heterologous transgenic plants." 1991, Mol Gen Genet, vol. 225 pp. 121-128.
Altenbach, S. B. et al., "Accumulation of a Brazil nut albmin in seeds of transgenic canola results in enhanced levels of seed protein methionine." 1992, Plant Molecular Biology, vol. 18, pp. 235-245.
Vandekerckhove, J. et al. "Enkephalins Produced in Transgenic Plants Using Modified 2S Seed Storage Proteins." 1989, Bio/Technology, vol. 7 pp. 929-932.
Roberts, B and Paterson, B. M. "Efficient Translation of Tobacco Mosaic Virus RNA and Rabbit Globi 9S RNA in a Cell-Free System from commercial Wheat Germ." 1973, Proc,. Nat. Acad. Sci. USA, vol. 70, pp. 2330-2334.
Kusnadi, A. R. et al., "Production and purification of Two Recombinant Proteins from Transgenic Com." 1998, Biotechnol. Prog., vol. 14, pp. 149-155.
Ong, Edgar, et al.; "Cloning and sequence analysis of two laccase complementary DNA's from the ligninolytic basidiomycete *Trametes versicolor*.", Gene;196:113-119 (1997).
Crestini, Claudia, et al.; "The early biodegeneration pathways of residual kraft lingin model compounds with laccase.", ISWPC (1997).
Bourbonnais, Robert, et al.; "Enzymztic delignification of craft pulp using laccase and a mediator", Tappi Journal, vol. 79:No. 6, Jun. (1996) p. 199-204.
Saloheimo, Markku, et al.; "Heterologous production of a ligninolytic enzyme: expression of the *Phlebia radiata* laccase gene in *Trichoderma reesei*", Bio/Thechnology vol. 9, Oct. 1991 p. 987-990.
Bourbonnais, Robert, et al.; "Lignin Oxidation by Laccase Isozymes from *Trametes versicolor* and role of the Mediator 2,2' -Azinobis(3-Ethlbenzthiazoline-6-Sulfonate) in kraft Lignin Depolymerization", Applied and Environmental Microbiology, May 1995, p. 1879-1880; vol. 61, No. 5.
Berka, Randy, et al.; "Characterization of the gene encoding an extracellular laccase of *Myceliphthora thermophila* and analysis of the recominant enzyme expressed in *Aspergillus oryzae*", Applied and Environmental Microbiology, Aug. 1997, p. 3151-3157; vol. 63, No. 8.

(Continued)

*Primary Examiner*—Anne Kubelik
(74) *Attorney, Agent, or Firm*—Genencor International, Inc.

(57) ABSTRACT

A method for commercial production and use of heterologous laccase from plant seed in commercial processes is shown. The method comprises degerminating the germ portion of the seed and using the germ as the source of laccase in a commercial process. Increased concentration of laccase on a dry weight basis is achieved. Increased cost recovery is obtained in the process.

18 Claims, 20 Drawing Sheets

OTHER PUBLICATIONS

Call, H.P., et al.; "History, overview and applications of mediated lignolytic systems, especially laccase-mediator-systems (Lignozym-Process)", Journal of Biotechnology 53 (1997) p. 163-202.

Yaropolov, A.I., et al.;"Laccase: Properties, Catalytic Machanism, and Applicability", Applied Biochemisty and biotechnology vol. 49, 1994 p. 257-280.

Amann, et al.; "The Lignozym Process- coming closer to the Mill", 1997 ISWPC.

"Technical and Market Opportunities for glued wood products", Adhesives Age May 31, 1996 p. 6-9.

Archibald, F.S., et al.; "Kraft pulp bleaching and delignification by Trametes Versicolor." Journal of Biotecnology, vol. 53 (1997) p. 215-236.

Solomon, Edward, et al.; "Multicopper Oxidases and Oxygenases", Chem. Rev 1996, 96, 2536-2605.

Kusnadi, A. R. et al., "Processing of Transgenic Corn Seed and its Effect on the Recovery of Recombinant B-Glucuronidase." 1998, Biotechnol. Bioengeneering, vol. 60, pp. 44-52.

Hood, E. E., et al.: "Commercial Production of avidin from Transgenic Maize", In Vitro,, vol. 32, No. 3, Jun. 27, 1996, pp. Pt. 2-67A.

Gallusci, P., et al.: "Differences in Cell Type-Specific Expression of the Gene Opaque 2 in Maize and Transgenic Tobacco", Molecular and General Genetics vol. 244, 1994, pp. 391-400.

Goldberg, R.B. et al, "Regulation of Gene Expression During Plant Embryogenesis", CELL, vol. 56, Jan. 27, 1989, pp. 149-160.

Skokut, T.A., et al.: "Expression of a Coriander Palmitoyl-ACP Delta 4 Desaturase in Transgenic Maize", Supplement to Plant Physiology vol. 111, No. 2, 1996, p. 167.

Cornejo, M-J., et al.: "Activity of a Maize Ubiquitin Promoter in Transgenic Rice", Plant Molecular Biology vol. 23, 1993, pp. 567-581.

Hood, E.E., et al., "Commercial Production of Gus from Transgenic Maize Seed", In Vitro vol. 33 No. 3, Jun. 14, 1997, pp. Pt 2-55A.

Bruce, et al. "Maize Uiquitin 1::Gus Expression in Transgenic Maize" In Vitro vol. 32 No. 3, Jun. 22-27, pp. 72A.

Holtorf et al. "Comparison of Different Constitutive and Inducible Promoters For the Overexpression of Transgenes in *Arabidopsis thaliana*" Plant Mol. Biol. 29:637-646, 1995.

Hood et al. "Commerical Production of Avidin From Transgenic Maize: Characterization of Transformat, Production, Processing, Extraction and Purification" Mol. Breeding 3:291-307 (1997).

Kusnadi et al. "Recovery of Recominant β-Glucuronidase from Transgenic Corn" The Proceedings of the 26$^{TH}$ Annual Biochemical Engineering Erickson, L.E., Ed.; Kansas State University, Manhattan Kansas pp. 143-152.

Kusnadi, et al. "Recovery of Recombinant β-Glucuronidase from Transgenic Corn" The Proceedings of the 26$^{TH}$ Annual Biochemical Engineering Erickson, L.E. Ed.: Kansas State University, Manhattan Kansas pp. 143-152 (1997) and orally presented Sep. 21, 1996.

* cited by examiner

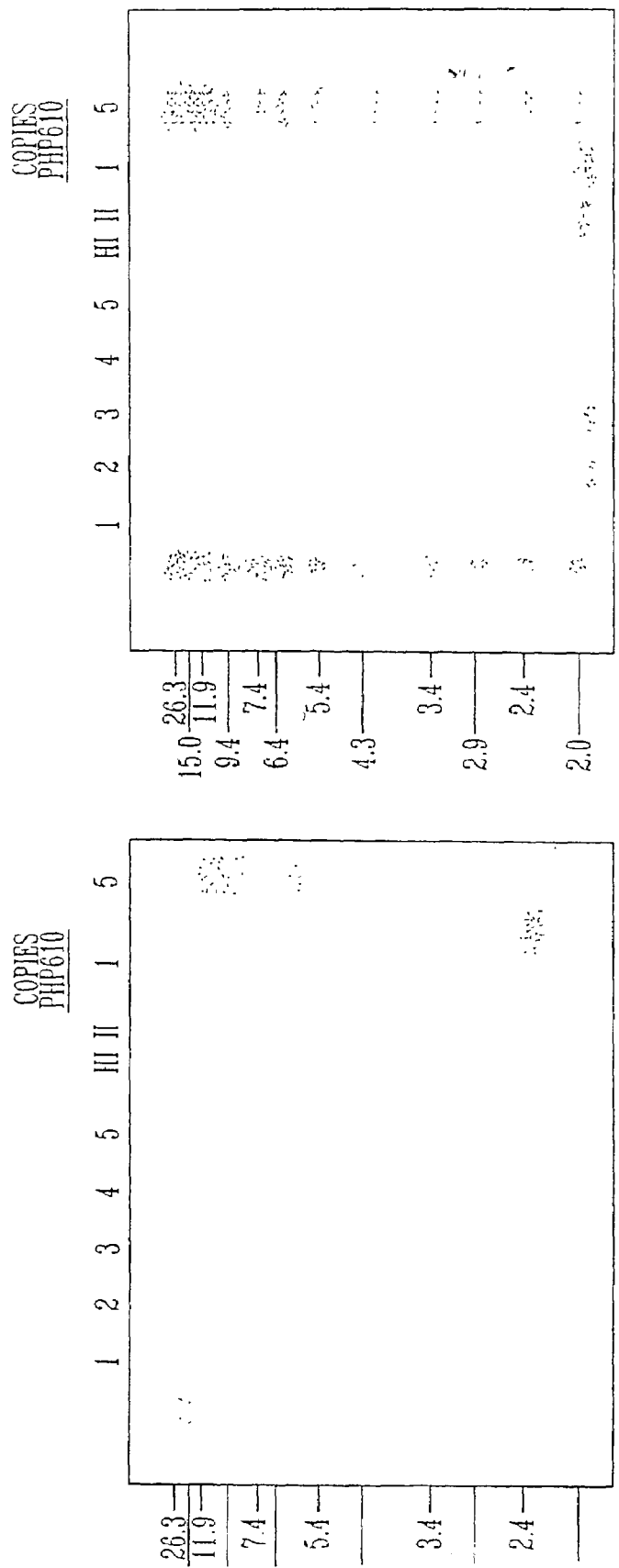

FIGURE 13A

```
     gccatcgggccggtggcgagcctcgtcgtcgcgaacgcccccgtctcgcccgacggcttc
  1  ------------+---------+---------+---------+---------+---------+   60
     cggtagcccggccaccgctcggagcagcagcgcttgcggggcagagcgggctgccgaag
     A  I  G  P  V  A  S  L  V  V  A  N  A  P  V  S  P  D  G  F cttcgggatgccatcgtggtcaacggcgtggtcccttccccgctcatcaccgggaagaag
 61  ------------+---------+---------+---------+---------+---------+  120
     gaagccctacggtagcaccagttgccgcaccagggaagggcgagtagtggcccttcttc
     L  R  D  A  I  V  V  N  G  V  V  P  S  P  L  I  T  G  K  K ggagaccgcttccagctcaacgtcgtcgacaccttgaccaaccacagcatgctcaagtcc
121  ------------+---------+---------+---------+---------+---------+  180
     cctctggcgaaggtcgagttgcagcagctgtggaactggttggtgtcgtacgagttcagg
     G  D  R  F  Q  L  N  V  V  D  T  L  T  N  H  S  M  L  K  S actagtatccactggcacggcttcttccaggcaggcaccaactgggcagacggacccgcg
181  ------------+---------+---------+---------+---------+---------+  240
     tgatcataggtgaccgtgccgaagaaggtccgtccgtggttgacccgtctgcctgggcgc
     T  S  I  H  W  H  G  F  F  Q  A  G  T  N  W  A  D  G  P  A ttcgtcaaccagtgccctattgcttccgggcattcatttctgtacgacttccatgtgccc
241  ------------+---------+---------+---------+---------+---------+  300
     aagcagttggtcacgggataacgaaggcccgtaagtaaagacatgctgaaggtacacggg
     F  V  N  Q  C  P  I  A  S  G  H  S  F  L  Y  D  F  H  V  P gaccaggcaggaacgttctggtaccacagtcatctgtctacgcaatactgtgacgggctg
301  ------------+---------+---------+---------+---------+---------+  360
     ctggtccgtccttgcaagaccatggtgtcagtagacagatgcgttatgacactgcccgac
     D  Q  A  G  T  F  W  Y  H  S  H  L  S  T  Q  Y  C  D  G  L cgaggaccgttcgtcgtgtacgaccccaaggatccgcacgccagccgctacgatgttgac
361  ------------+---------+---------+---------+---------+---------+  420
     gctcctggcaagcagcacatgctggggttcctaggcgtgcggtcggcgatgctacaactg
     R  G  P  F  V  V  Y  D  P  K  D  P  H  A  S  R  Y  D  V  D aacgagagcacggtcatcacgttgaccgactggtaccacaccgctgcccggctcggtccc
421  ------------+---------+---------+---------+---------+---------+  480
     ttgctctcgtgccagtagtgcaactggctgaccatggtgtggcgacgggccgagccaggg
     N  E  S  T  V  I  T  L  T  D  W  Y  H  T  A  A  R  L  G  P
```

FIGURE 13B

```
    aggttcccactcggcgcggacgccacgctcatcaatggtcttgggcggtcggcctccact
481 ---------+---------+---------+---------+---------+---------+ 540
    tccaagggtgagccgcgcctgcggtgcgagtagttaccagaacccgccagccggaggtga
     R  F  P  L  G  A  D  A  T  L  I  N  G  L  G  R  S  A  S  T cccaccgccgcgcttgctgtgatcaacgtccagcacggaaagcgctaccgcttccgtctc
541 ---------+---------+---------+---------+---------+---------+ 600
    gggtggcggcgcgaacgacactagttgcaggtcgtgcctttcgcgatggcgaaggcagag
     P  T  A  A  L  A  V  I  N  V  Q  H  G  K  R  Y  R  F  R  L gtttcgatctcgtgcgacccgaactacacgttcagcatcgacgggcacaatctgaccgtc
601 ---------+---------+---------+---------+---------+---------+ 660
    caaagctagagcacgctgggcttgatgtgcaagtcgtagctgcccgtgttagactggcag
     V  S  I  S  C  D  P  N  Y  T  F  S  I  D  G  H  N  L  T  V atcgaggtcgacggtatcaacagccagcctctccttgtcgactctatccagatcttcgcc
661 ---------+---------+---------+---------+---------+---------+ 720
    tagctccagctgccatagttgtcggtcggagaggaacagctgagataggtctagaagcgg
     I  E  V  D  G  I  N  S  Q  P  L  L  V  D  S  I  Q  I  F  A gcgcagcgctactcctttgtgttgaatgcgaaccaaacggtcggcaactactgggtccgc
721 ---------+---------+---------+---------+---------+---------+ 780
    cgcgtcgcgatgaggaaacacaacttacgcttggtttgccagccgttgatgacccaggcg
     A  Q  R  Y  S  F  V  L  N  A  N  Q  T  V  G  N  Y  W  V  R gcgaacccgaacttcggaacggttgggttcgccggggggatcaactccgccatcctgcgc
781 ---------+---------+---------+---------+---------+---------+ 840
    cgcttgggcttgaagccttgccaacccaagcggccccctagttgaggcggtaggacgcg
     A  N  P  N  F  G  T  V  G  F  A  G  G  I  N  S  A  I  L  R taccaaggcgcaccagtcgccgagcccactacgacccagacgacgtcggtgatcccgctt
841 ---------+---------+---------+---------+---------+---------+ 900
    atggttccgcgtggtcagcggctcgggtgatgctgggtctgctgcagccactagggcgaa
     Y  Q  G  A  P  V  A  E  P  T  T  T  Q  T  T  S  V  I  P  L atcgagacgaacttgcacccctcgctcgcatgcctgtgcctggcagcccgacacccggg
901 ---------+---------+---------+---------+---------+---------+ 960
    tagctctgcttgaacgtggggagcgagcgtacggacacggaccgtcgggctgtgggccc
     I  E  T  N  L  H  P  L  A  R  M  P  V  P  G  S  P  T  P  G ggcgtcgacaaggcgctcaacctcgcgtttaacttcaacggcaccaacttcttcatcaac
961 ---------+---------+---------+---------+---------+---------+ 1020
    ccgcagctgttccgcgagttggagcgcaaattgaagttgccgtggttgaagaagtagttg
     G  V  D  K  A  L  N  L  A  F  N  F  N  G  T  N  F  F  I  N
```

FIGURE 13C

```
         aacgcgactttcacgccgccgaccgtcccggtactcctccagattctgagcggtgcgcag
1021     ---------+---------+---------+---------+---------+---------+   1080
         ttgcgctgaaagtgcggcggctggcagggccatgaggaggtctaagactcgccacgcgtc
         N  A  T  F  T  P  P  T  V  P  V  L  L  Q  I  L  S  G  A  Q accgcacaagacctgctccctgcaggctctgtctacccgctcccggcccactccaccatc
1081     ---------+---------+---------+---------+---------+---------+   1140
         tggcgtgttctggacgagggacgtccgagacagatgggcgagggccgggtgaggtggtag
         T  A  Q  D  L  L  P  A  G  S  V  Y  P  L  P  A  H  S  T  I gagatcacgctgcccgcgaccgccttggccccgggtgcaccgcacccttccacctgcac
1141     ---------+---------+---------+---------+---------+---------+   1200
         ctctagtgcgacgggcgctggcggaaccggggcccacgtggcgtggggaaggtggacgtg
         E  I  T  L  P  A  T  A  L  A  P  G  A  P  H  P  F  H  L  H ggtcacgccttcgcggtcgttcgcagcgcggggagcaccacgtataactacaacgacccg
1201     ---------+---------+---------+---------+---------+---------+   1260
         ccagtgcggaagcgccagcaagcgtcgcgcccctcgtggtgcatattgatgttgctgggc
         G  H  A  F  A  V  V  R  S  A  G  S  T  Y  N  Y  N  D  P atcttccgcgacgtcgtgagcacgggcacgcccgccgcgggcgacaacgtcacgatccgc
1261     ---------+---------+---------+---------+---------+---------+   1320
         tagaaggcgctgcagcactcgtgcccgtgcgggcggcgcccgctgttgcagtgctaggcg
         I  F  R  D  V  V  S  T  G  T  P  A  A  G  D  N  V  T  I  R ttccagacggacaaccccgggccgtggttcctccactgccacatcgacttccacctcgac
1321     ---------+---------+---------+---------+---------+---------+   1380
         aaggtctgcctgttggggcccggcaccaaggaggtgacggtgtagctgaaggtggagctg
         F  Q  T  D  N  P  G  P  W  F  L  H  C  H  I  D  F  H  L  D gcgggcttcgcgatcgtgttcgcagaggacgttgcggacgtgaaggcggcgaacccggtt
1381     ---------+---------+---------+---------+---------+---------+   1440
         cgcccgaagcgctagcacaagcgtctcctgcaacgcctgcacttccgccgcttgggccaa
         A  G  F  A  I  V  F  A  E  D  V  A  D  V  K  A  A  N  P  V ccgaaggcgtggtcggacctgtgcccgatctacgacgggctgagcgaggctaaccagtga
1441     ---------+---------+---------+---------+---------+---------+   1500
         ggcttccgcaccagcctggacacgggctagatgctgcccgactcgctccgattggtcact
         P  K  A  W  S  D  L  C  P  I  Y  D  G  L  S  E  A  N  Q  *
```

METHODS FOR COMMERCIAL PRODUCTION OF HETEROLOGOUS LACCASE IN PLANT TISSUE AND EXTRACTION OF THE LACCASE FROM PLANT SEED

This application is a continuation-in-part of U.S. application Ser. No. 09/403,686, filed Sep. 7, 1999, now U.S. Pat. No. 6,504,085, which is a section 371(c) filing from PCT/US97/04526, filed Mar. 20, 1997, which claims priority to U.S. Application Ser. No. 60/040,119 filed Mar. 7, 1997. The contents of all of these applications are fully incorporated herein by reference in their entirety, as are all other references cited herein.

FIELD OF THE INVENTION

The present invention is to commercial production of proteins in plants, and in particular commercial production of laccase in plants, and to use of such proteins in commercial applications.

BACKGROUND OF THE INVENTION

For decades, many proteins useful to humans or animals have been isolated from plants. With the advent of genetic engineering technology, a plant could be modified to produce human, animal, viral, bacterial, or fungal proteins. Transgenic plants offer the potential to be one of the most economical systems for large-scale production of proteins for industrial, pharmaceutical, veterinary and agricultural use. Advantages of plant systems include the low cost of growing a large biomass, easy scale-up (increase of planted acreage), natural storage organs (tubers, seeds), and established practices for efficient harvesting, transporting, storing, and processing of the plant. Recombinant proteins can be targeted to seeds allowing stable storage of the recombinant proteins for extended periods. Plants offer advantages over other production systems since some proteins may be used without extensive purification, because for many applications, plant material is used directly as a food source or feed stock.

Examples abound for expression of foreign genes in plants Benfey P N, Chua N—H: Regulated genes in transgenic plants. *Science* 244:174–181 (1989); Fisk H J, Dandekar A M: The introduction and expression of transgenes in plants. Scientia Hort. 55:5–36 (1993). In general, the expression of these foreign genes has been aimed at benefiting the consumer through plant improvement by: a) expressing antifungal compounds or growth factors; b)improving agronomic traits such as fruit ripening or nutritional contents or c) inducing sterility in the context of creating hybrid plants. It is also feasible to express in plants heterologous genes that encode high value products, a technology currently being explored by several plant biotechnology companies and university laboratories. In many cases, expression in plants could be the system of choice because of such inherent advantages as cost relative to that of animal tissue culture, and the concern that prokaryotic or yeast expression systems may not be capable of correct glycosylation and other post-translational processing steps required for proper function of the expressed protein Pen J, Sijmons P C, van Ooijen A J J, Hoekema A: Protein production in transgenic crops: Analysis of plant molecular farming. Industrial Crops Production. Elsevier, Amsterdam. pp. 241–250 (1993B). Thus, there is a need to improve such systems for increased efficiency of expression of the protein and to lower production costs. Among representative efforts to achieve such goals is the Goodman et al patent assigned to Calgene, U.S. Pat. No. 5,550,038, which discloses constructs for expression of physiologically active mammalian proteins in plant cells. The isolation and purification procedure for the mammalian peptides disclosed there is to preparation from frozen tobacco tissue obtained from tissue culture which is ground in liquid nitrogen, centrifuged, washed with ethylene glycol and dialyzed overnight in dialysis buffer to obtain γ-IFN.

Vanderkerckhove et al, assigned to Plant Genetic Systems N.V, at U.S. Pat. No. 5,487,991, discloses a method for producing polypeptides by cultivating a plant whose genome contains recombinant DNA. Recovery of transgenic proteins is accomplished by harvesting seeds from cultivated plants, cleaving out the peptide of interest and recovering the peptide of interest in a purified form. The recovery of the active polypeptides involves homogenizing the entire seed in dry ice and extraction with hexane, extraction with high salt buffer and dialysis against distilled water and precipitating the contaminating globulins. Further purification is accomplished by gel-filtration chromatography, and finally ion-exchange chromatography.

The extraction process shown at PCT WO92/010402 by Willmitzer et al and assigned to Novo Nordisk provides for homogenizing plant tissue and use of extraction buffer, filtration and centrifugation.

In PCT WO95/14099 by Rodriguez et al, assigned to the University of California, methods for production and secretion of heterologous proteins in plants are discussed wherein malting monocot plant seeds is disclosed to stimulate heterologous protein production in cereal seeds, causing conversion of the endosperm to maltose and germination of the seeds. The chimeric gene includes a transcriptional regulatory region inducible during seed germination, a DNA sequence encoding a protein of interest and further contains a signal sequence linked to the transcriptional regulatory region effective to facilitate secretion of the protein across the aleurone or scutellar epithelium layer into the endosperm. In one embodiment, the embryos and endosperm may be separately steeped in 55° F. water for 48 hours followed by four day germination in bins or drums with inducement of a promoter or addition of plant hormones. This is because expression in the embryo was poor unless different conditions were used to cause induction of the protein in the embryo versus the endosperm. The embryo and endosperm portions are then mixed and mashed.

Factors that can be manipulated to control levels of expression are the presence of transcriptional modification factors such as introns, polyadenylation signals and transcription termination sites. Intron sequences within the gene of interest also may increase its expression level by stabilizing the transcript and allowing its effective translation. Many plant genes contain intron sequences exhibiting this positive impact on expression (Callis J, Fromm M, Walbot V: Introns increase gene expression in cultured maize cells. Genes and Development 1:1183–1200 (1987)) including for example some of the plant ubiquitin genes Christensen A M, Sharrock R A, Quail P H: Maize polyubiquitin genes: structure, thermal perturbation of expression and transcript splicing, and promoter activity following transfer to protoplasts by electroporation. Plant Mol. Biol. 18:675–689 (1992); Christensen A M, Sharrock R A, Quail P H: Maize polyubiquitin genes: structure, thermal perturbation of expression and transcript splicing, and promoter activity following transfer to protoplasts by electroporation. Plant Mol. Biol. 18:675–689 (1992) and the Adh2 gene (Callis, supra). At the translational level, factors to consider that affect expression level of foreign genes are the ribosomal binding site and the codon bias of the gene [Cornejo M, Luth D, Blankenship K, Anderson O, Blechl A: Activity of a maize ubiquitin promoter in transgenic rice. Plant Mol. Biol. 23: 567–581 (1993) and references therein]. High-level expression of a gene product which accumulates in the cytoplasm may result in toxicity to the plant cell. Therefore, sequestering the protein into a compartment (organelle) or transporting it to the extracellular matrix may allow higher expression levels. Efforts are being made to understand plant protein targeting (An G, Mitra A, Choi H K, Costa M A, An K, Thornburg R W, Ryan C A: Functional analysis of the 3' control region of the potato wound-inducible proteinase inhibitor II gene. Plant Cell 1:115–122 (1989); Jones R L, Robinson D G: Protein secretion in plants. New-Phytol. New York, N.Y.: Cambridge University Press. April 1989. v. 111 (4) p. 567–597. ill) and proteins can be effectively targeted to the mitochondrion, the chloroplast, the vacuole, peroxisomes or the cell wall. The specific choice of where to target will depend on the nature of the protein of interest and the specific need. Insertion of a construct at different loci within the genome has been observed to cause variation in the level of gene expression in plants. The effect is believed to be due at least in part to the position of the gene on the chromosome, producing individual isolates with different expression levels (Staehelin L A, Moore I: The plant golgi apparatus: Structure, functional organization and trafficking mechanisms. Ann. Rev. Plant Physiol. Plant Mol. Biol. 46:261–288 (1995)).

One of the critical factors in expression of protein in plants is the choice of transcriptional promoters used. The range of available plant compatible promoters includes tissue-specific and inducible promoters. Some of the better documented constitutive promoters include the CaMV 35s promoter and its tandem arrangement, as described in European patent application number 0 342 926, and the ubiquitin promoter, as disclosed in Quail et al, assigned to Mycogen Plant Science, Inc. U.S. Pat. No. 5,510,474.

The invention here improves on what has been known through the determination that the germ can be separated from the endosperm, not for enriching the endosperm fractions, but to be used separately for recovery of protein and high activity obtained. The germ (which is the term for the embryo used in commercial plant production) is surprisingly found to have an enhanced concentration level of protein on a dry weight basis. Thus, only a small amount of tissue is needed to provide high levels of protein expression. This provides for considerable cost savings, as the separated endosperm and other parts of the seed can be sold for food, feed, and other commercial processing and the much smaller germ material as opposed to the entire seed is used, producing more protein per material processed. Commercial production of protein from plant biofactories has not previously considered use of the germ as the protein source; instead those in the field desired to use the entire seed as the source of protein, since presumably it would yield higher amounts of protein available for the commercial process to which it would be applied. Instead, the inventors have found that the germ not only can be the source of the protein, but is a more desirable source of the protein.

The protein can be extracted from the germ, or the germ tissue can be used directly in the commercial process. In the latter situation, cost of the protein production is even further decreased. In one embodiment, laccase can be produced in plants and the germ used as the source of the enzyme. The germ can be used directly in commercial processes where laccase is useful.

Further, expression of protein can be directed to the germ, further enhancing protein recovery. For example, the ubiquitin promoter, believed to have been constitutively expressed, greatly increases expression of protein in the germ.

The present invention relates, in general, to a novel method of catalyzing in vitro reactions using transgenic plant germ tissues that over-express a desired protein. More specifically, the present invention relates to the enzymatic polymerization of lignin based compositions with laccase enzymes. The present invention also pertains to a method of enhancing the biochemical availability of laccase.

Laccases (E.C. 1.10.3.2) are polyphenol oxidizing enzymes. They are blue copper oxidases in that they contain a copper atom or atoms as a prosthetic group. Together, laccases and the aromatic residues of lignin can produce reactive groups in the lignin molecule in a kind of radical phenol-oxidation reaction, whereby these groups then polymerize and/or cross-link in secondary reactions. Laccases are known from plants, fungi and animal sources. The main source of laccase for commercial purposes is fungi such as the basidiomycetes *Phanerochaete chrysosporium* and *Trametes versicolor*. Other fungi producing laccase include *Aspergillus, Neurospora, Botrytis, Polyporus, Pleurotus, Philota, Podospora, Collybia* and *Rhizoctonia*.

The uses of laccases are numerous. Examples include catalyzing the oxidation of compounds such as o,p-diphenols, aminophenols, polyphenols, polyamines, and inorganic ions (Yaropolov et al. 1994. *Applied Biochemistry and Biotechonology* 49:257–280). The use of laccases as marker enzymes in enzyme immunoassays (EIA) has also been discussed, as well as their use in the oxidation of steroids and synthesis of vinblastine, a cytostatic compound used in treating malignant diseases. Laccase can also be used in gelling reactions. Bolle and Aehle in a U.S. Pat. No. 6,217,942 to Genencor International, Inc. describe a method of using laccase for the production of a coated article from the waste liquors produced by the pulp and paper industry. The method comprises: (a) preparing a solution of lignin, said solution preferably comprising lignin sulfonate, (b) mixing the lignin solution with a phenol oxidizing enzyme, preferably laccase, (c) incubating the mixture under conditions sufficient to form a solution of desired viscosity, (d) contacting or spreading the mixture from step (c) on an article to be coated, and (e) allowing the film to set onto the article by subjecting the article to conditions and for a time sufficient to form a film on the surface of the article.

A common use of laccase is in connection with the paper and pulp industry. Lignin is a rigid organic polymer and harsh physiochemical conditions must be used to attack or modify the substance. Naturally occurring white rot fungi destroy lignin using laccases and peroxidases. In plants, laccases are localized in woody tissues and cell walls of herbaceous species and it is believed it participates in lignin biosynthesis. It is involved in breaking down lignin as well as creating lignin polymers. It is also especially useful as a "biological glue" or adhesive or binder when manufacturing glued wood products. Such products include construction and industrial plywood, oriented strand board, particleboard and medium density fiberboard.

Currently, the adhesive mostly used is either a urea-formaldehyde type or a phenol-formaldehyde resin. There are disadvantages associated with use of formaldehyde in producing such products. Processing and end use monitoring are required as the levels of formaldehyde cannot exceed certain controls. Thus, there has been considerable interest in using such natural alternatives as laccase. It is reported that more than 1.2 million metric tons of adhesive resin solids are used to bond glued wood products in the United States. Which adhesive is used is driven by cost per unit of production, process compatibility and end-use durability (Technical and Market Opportunities for Glued Wood Products" *Adhesive Age* May 31, 1996 V39, N6 p.609).

An example of such a process is described by Kharazipour et al in U.S. Pat. No. 5,505,772 and by Olesen et al. at U.S. Pat. No. 5,618,482. In general, fibers and chips from wood or wood-like materials are defibrated by mechanical, steam, or other process. Laccase is then brought into contact with the material in a solution that may contain various auxiliary elements. Since laccase is a large molecule, a mediator may be utilized to aid the enzyme activity in penetrating the wood and may be added to the solution. The mix is incubated and may then be shaped into formed boards.

There has also been some interest in the field for enhancing laccase activity and/or stability in in-vitro reactions. One example is described by Schneider et al in a U.S. Pat. No. 5,795,855 to Novo Nordisk A/S. This patent discusses methods for enhancing laccase activity using organic chemical compounds. These chemical compounds consist of at least two aromatic rings, of which at least one ring is substituted with one or more of the following atoms: nitrogen, oxygen, and sulfur; and which aromatic rings may furthermore be fused rings. They report that the addition of such enhancers leads to a much faster bleaching of a dye (Direct Blue 1). It is obvious, therefore, that enhancing the biochemical activity of laccase is a sought-after invention that could be useful for various industries. Laccase production in plants does that without the use of environmentally polluting chemicals.

The compound ABTS (2,2'-azino-bis(3-ethylbenzothiazoline-6-sulfonate), supplied by Boehringer Mannheim, has been proposed to act as a redox mediator for oxidation of non-phenolic lignin model compounds (Bourbonnais and Paice. 1990. FEBS Lett. 267: 99–102). Studies on demethylation and delignification of kraft pulp by a laccase showed that the extent of partial demethylation by laccase was increased in the presence of ABTS (Bourbonnais and Paice. 1992. Appl. Microbiol. Biotechnol. 36: 823–827). Other accelerators or enhancers have also been described. Metal ions, phenolic compounds such as 7-hydroxycoumarin, vanillin and p-hydroxybenzenesulfonate, have been described as compounds capable of enhancing bleaching reactions (WO 9218683, WO 9218687).

An effect of plant substances on enzyme performance has been reported by Lacki and Duvnjak (1999) Stability of polyphenol oxidase from the white-rot fungus *Trametes versicolor* in the presence of canola meal. *Acta Biotechnol.* 19:2, 91–100.). The authors found that canola meal improves the thermal stability of a polyphenol oxidase. The authors, however, did not report any enhancement in the activity or availability of the polyphenol oxidase in the presence of canola meal.

U.S. Pat. No. 5,543,576 presents a method of catalyzing in vitro reactions using transgenic seeds containing enhanced amounts of enzymes. The method involves directly adding transgenic seeds, preferably in a ground form, to a reaction mixture. The process uses whole seeds and does not disclose use of germ plant tissue as source of the enzyme. By use of the germ, less tissue is needed to obtain higher concentration on a dry weight basis, providing cost advantages, recovery of costs from sale of the other portions of the seed, and less tissue which needs to be stored, handled and processed.

Thus it is an object of the invention to decrease cost in production of commercial protein through using germ of seed expressing the protein in commercial processes.

An object of the invention is to use seed for production of commercial protein more efficiently.

It is another object of the invention to use the germ portion of the seed for production of commercial protein while retaining high activity of the recombinant protein.

Another object of the invention is to increase concentration of heterologous protein in plant tissue on a dry weight basis by using the germ as the source of the protein.

A still further object of the invention is to direct expression of heterologous protein in a seed to the germ or embryo portion of the seed.

An additional object of the invention is to provide a safe method for storing and handling heterologous proteins produced in plants. The germ matrix protects the enzyme from degradation due to endogenous protease inhibitors and the desiccated form of the germ. The germ matrix stabilizes the enzyme while still leaving it available to react with the substrates.

Yet another object of the invention is to increase concentration of heterologous laccase produced in plant tissue on a dry weight basis by using the germ as the source of laccase.

Another object of the invention is to use germ as the source of heterologous laccase by addition of the germ in a commercial process.

A further object of the invention is to overcome limitations on the amount of laccase available in commercial processes when the laccase is produced in plants due to the discovery that a certain amount of laccase cannot be removed from plant cells. Instead, the germ tissue is used in the process, making all the laccase contained in the tissue available.

The foregoing objectives and others will become apparent in the description below.

SUMMARY OF THE INVENTION

The germ of a plant seed is separated from the rest of the seed into which a heterologous gene encoding a protein has been introduced. The protein is produced in a plant which is capable of degermination in a commercial milling process. The germ is used as the source of the protein in a commercial process. In one embodiment, the heterologous protein produced is laccase. The laccase-containing germ may be used directly in a commercial process in which laccase is required.

BRIEF DESCRIPTION OF THE DRAWINGS

FIG. 2: DNA blot hybridization analysis of avidin-1 plants with the avidin gene specific probe (A) or the bar gene specific probe (B). A. DNA was extracted from five plants (T1 generation). The DNA was digested with SphI and SpeI to generate fragments within the plant transcription unit. Three plants were positive in this hybridization experiment.

Lanes 1–5 represent individual plants. Copies 1 and 5 refer to plasmid DNA loaded in one and five copy number reconstructions. The intensity and number of bands indicate the number of copies of the gene in the transgenic plant. B. DNA from the same preps as in A was digested with EcoRI and XbaI to generate fragments within the plant transcription unit. Information from this blot indicates the number of copies of the gene in the transgenic plant. Lanes are the same as in A.

FIG. 3: Tissue prints of near mature kernels from an avidin-positive plant (A–C) or an avidin-negative plant (D). A. Tissue print stained for total protein with India ink. B, C. Tissue prints incubated with the anti-avidin antibody (ICN, 1:1000 dilution) and an alkaline phosphatase conjugated secondary antibody (Sigma Chemical Co., 1:1000 dilution). Note high concentration of avidin protein in the embryo (E). D. Avidin-negative kernel tissue print incubated as in B and C. Ax, embryonic axis; Sc, scutellum; En, endosperm. Bars represent 1 mm.

FIG. 4: Localization of avidin protein in the embryo at the light microscope level. A. Phase contrast image of embryonic axis. B. Rhodamine (TRITC) fluorescence of same image as in A. Double arrows mark similar locations in each image. Bar represents 10 µm.

Figure 5:
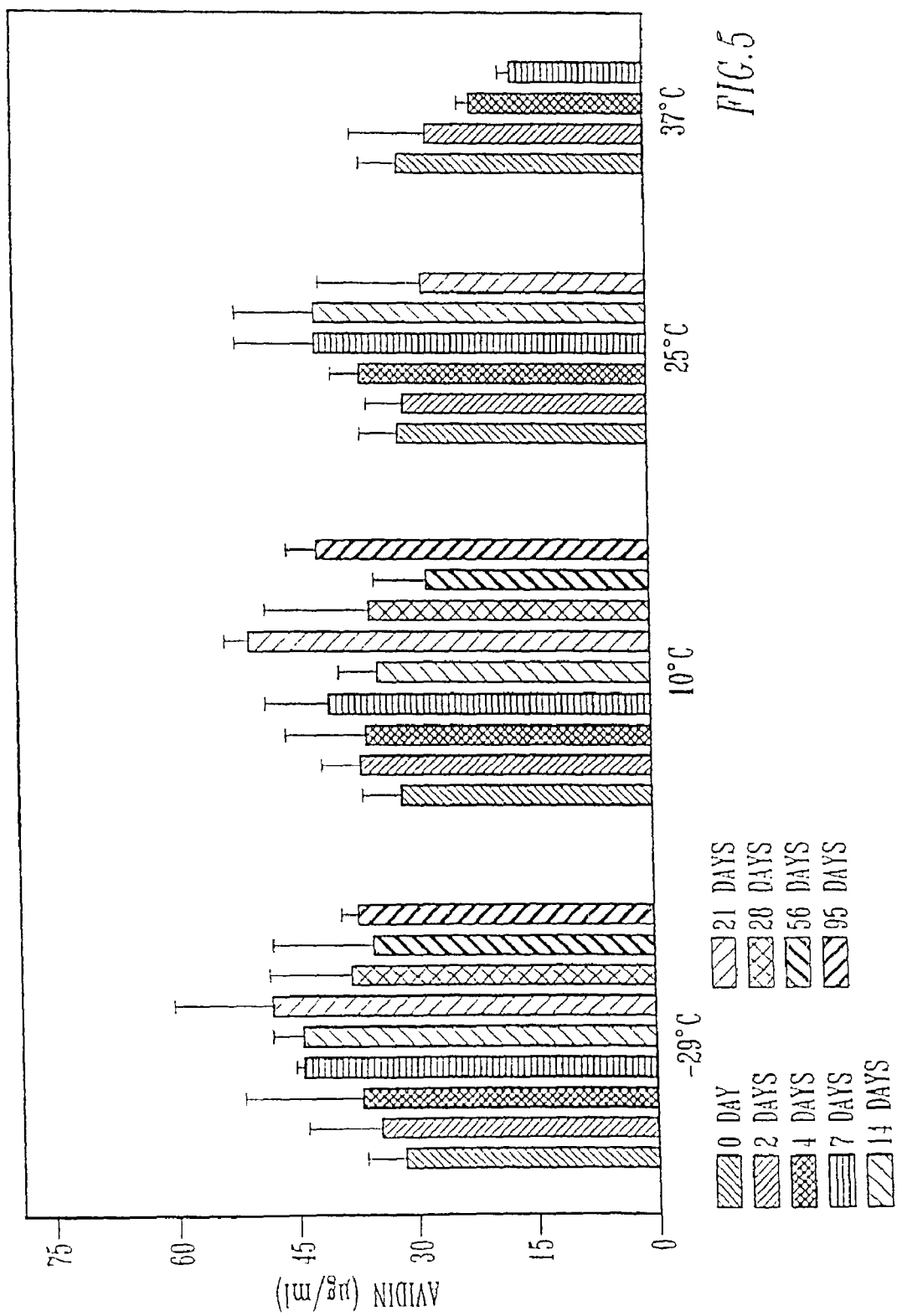

FIG. 5: Effect of temperature on avidin stability during storage of flaked maize seed. Maize seed was processed by cracking and flaking, then stored at the indicated temperatures. Triplicate samples were extracted and analyzed for avidin binding activity after the times (in days) shown by the shaded bars. Bars represent means with standard deviations indicated by the vertical bars.

Figure 6:
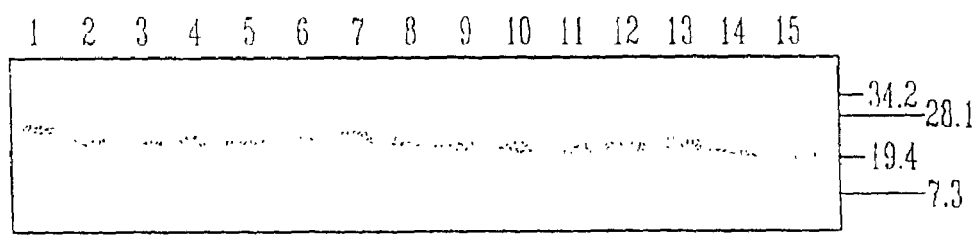

FIG. 6: Western blot of extracts of flaked maize seed in the presence of and absence of protease inhibitors. Lanes: 1, 4, 7, 10 and 13—native avidin after 0, 1, 3, 6 and 22 h without inhibitors. Lanes: 2, 5, 8, 11 and 14—maize extracts after 0, 1, 3, 6 and 22 h without inhibitors. Lanes: 3, 6, 9, 12, and 15—maize extracts after 0, 1, 3, 6 and 22 h with inhibitors.

Figure 7A:
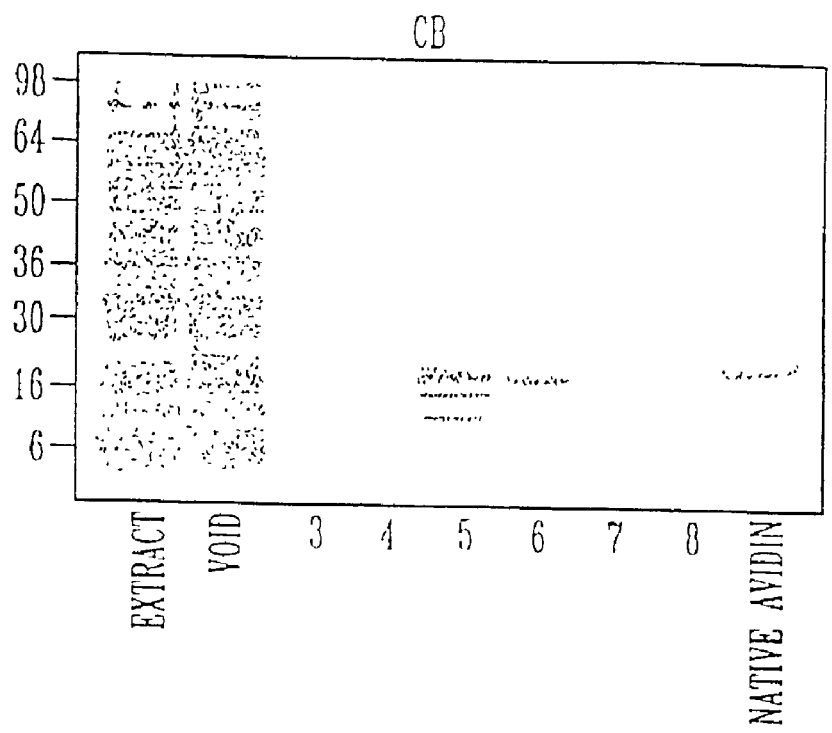
Figure 7B:
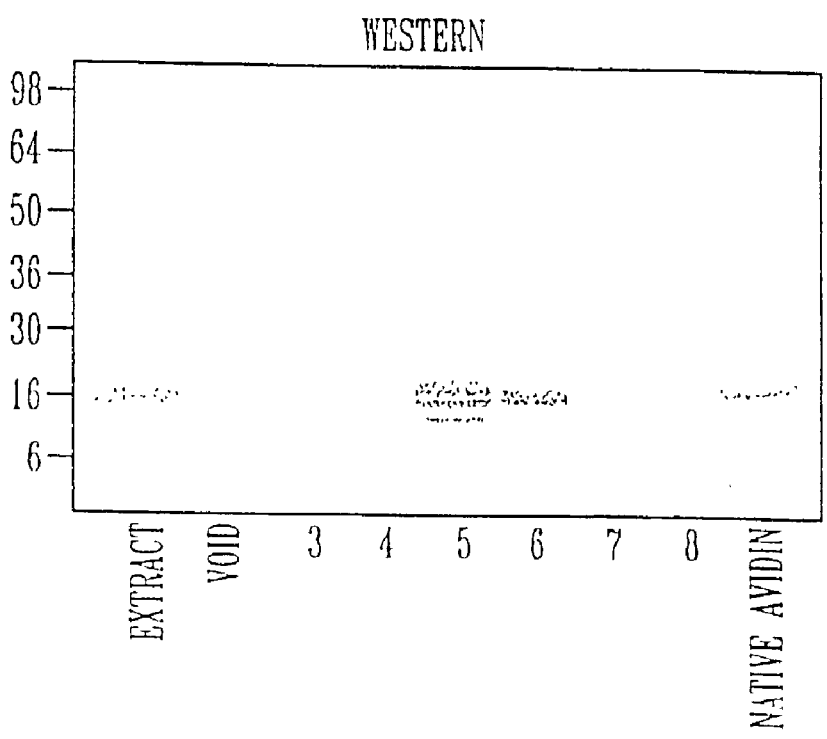

FIG. 7: Purification of recombinant avidin from maize seed extract. . A. Coomassie Blue (CB) stained 4–20% polyacrylamide gel of: Lanes:—10 µl of avidin positive corn extract (Extract),10 µl of column void (Void), 4 µl of column elution fractions 3–8 (lanes 3–8). and 2 µg of native avidin (native avidin). B. Immunoblot stained with affinity-purified polyclonal antibody against avidin: Lanes—µl of avidin positive corn extract (Extract), 10 µl of column void (Void), 2 µl of column elution fractions 3–8 (lane 3–8), and 1 µg of native avidin (native avidin). Molecular weight standards ($\times 10^{-3}$) are indicated on the left.

Figure 8A:
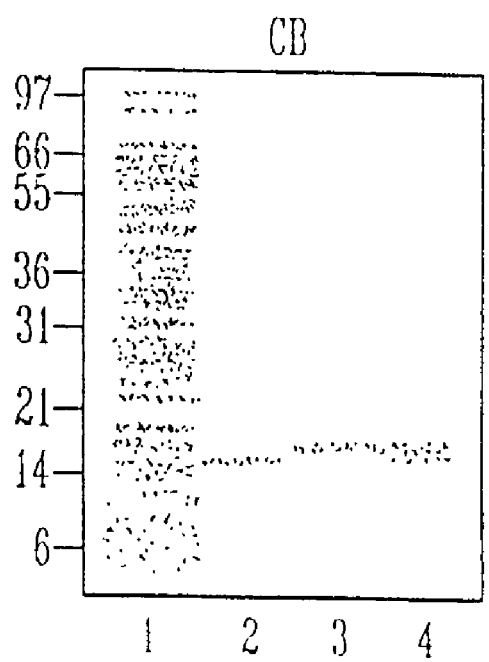
Figure 8B:
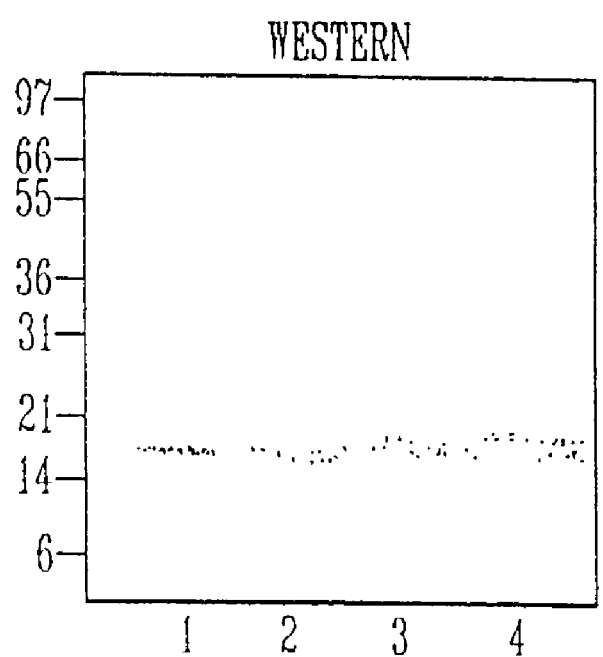

FIG. 8: Comparison between recombinant avidin and native avidin. A. Coomassic blue (CB) stained 4–20% polyacrylamide gel of: Lanes: 1.20 µg avidin-positive maize seed extract; 2.1 µg of recombinant avidin; 3.1 µg of native avidin; and 4.0.5 µg each of native and recombinant avidin. B. Western blot (WB) stained with affinity-purified polyclonal antibody raised against avidin. Lanes: 1.20 µg of avidin positive seed extract; 2.0.5 µg of recombinant avidin: 3.0.5 µg of native avidin and 4.0.5 µg each of recombinant and native avidin. Molecular weight standards ($\times 10^{-3}$) are indicated on the left.

Figure 9:
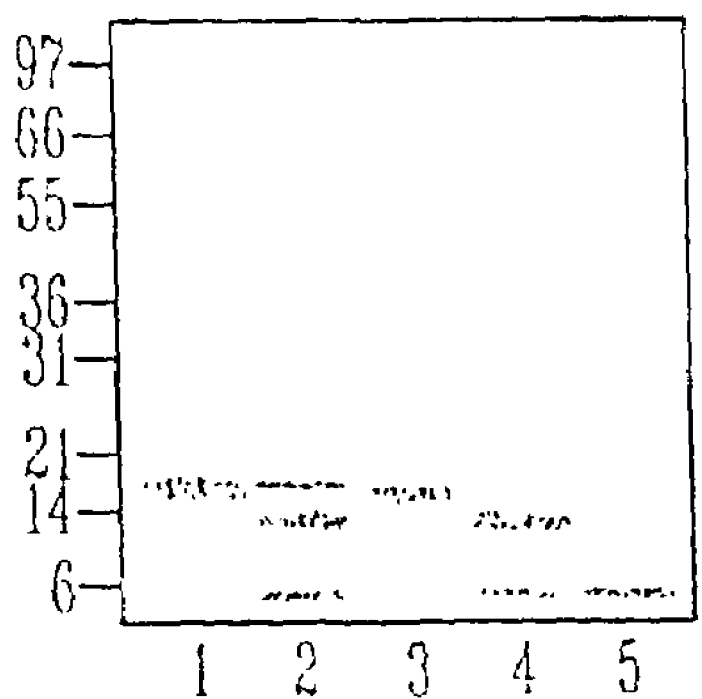

FIG. 9: Deglycosylation of avidin. Native avidin (2 µg) was incubated overnight at 37° C. in the absence (lane 1) or presence (lane 2) of 0.5 m units of N-glycosidase A (NGA). Recombinant avidin (2 µg) was also incubated overnight at 37° C. in the absence (lane 3) or presence (lane 4) of 0.5 m units of NGA. Lane 5 contains 0.5 units of NGA incubated overnight at 37° C. The 4–20% polyacrylamide gel was stained with Coomassie blue. Molecular weight standards ($\times 10^{-3}$) are indicated on the left.

Figure 10A:
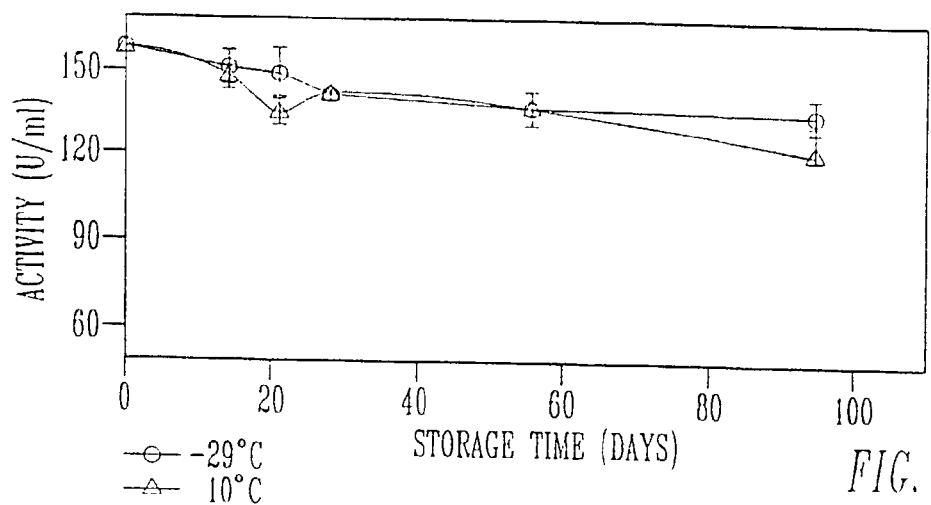
Figure 10B:
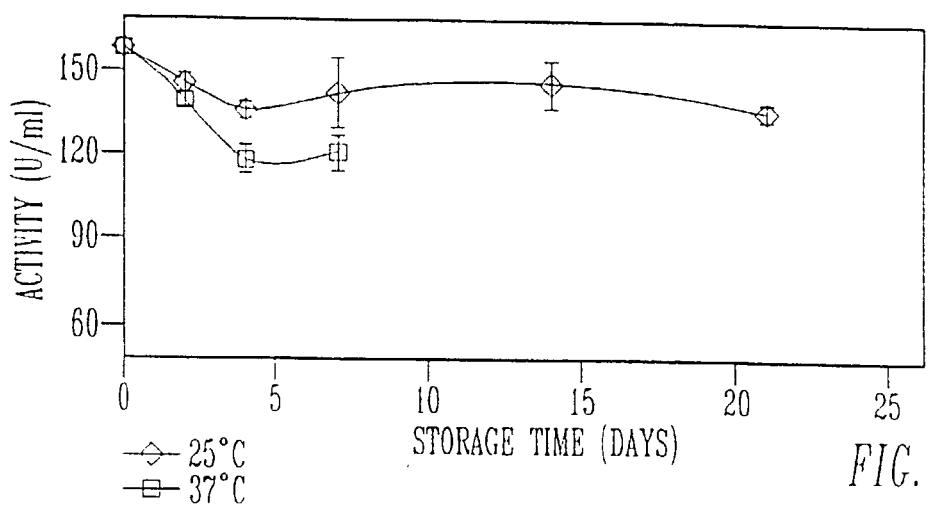

FIG. 10 are graphs showing storage stability of rGUS in flaked corn.

Figure 11A:
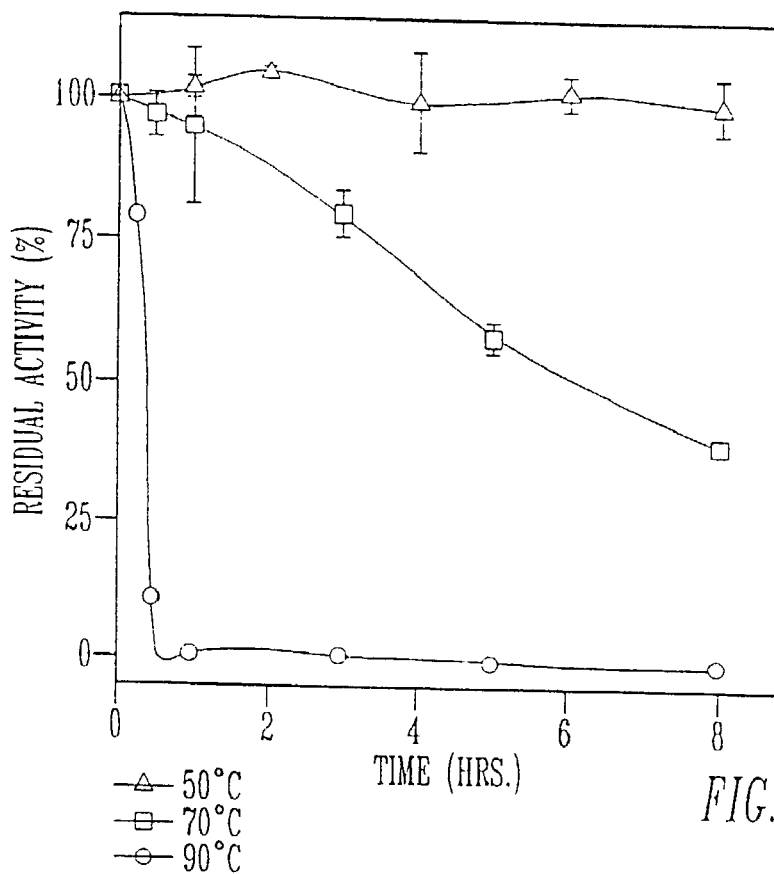
Figure 11B:
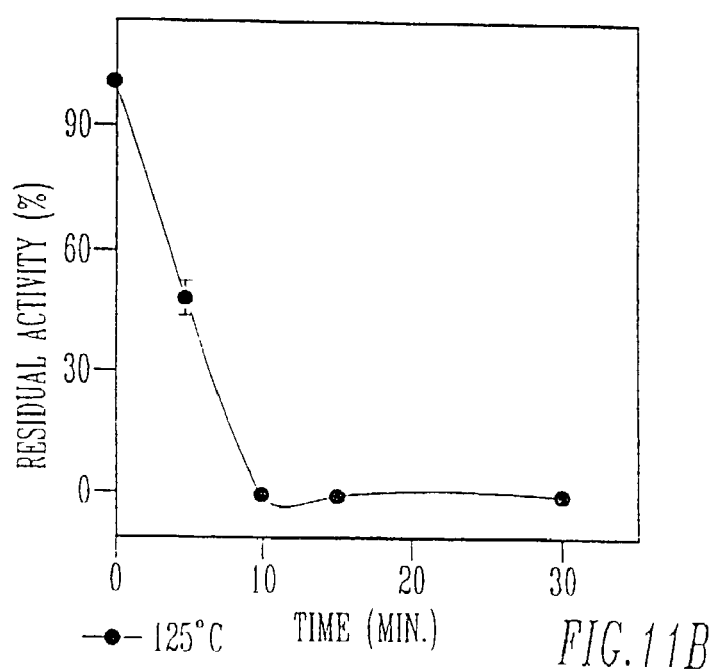

FIG. 11 is graph depicting heat stability of rGUS in corn kernels.

Figure 12:
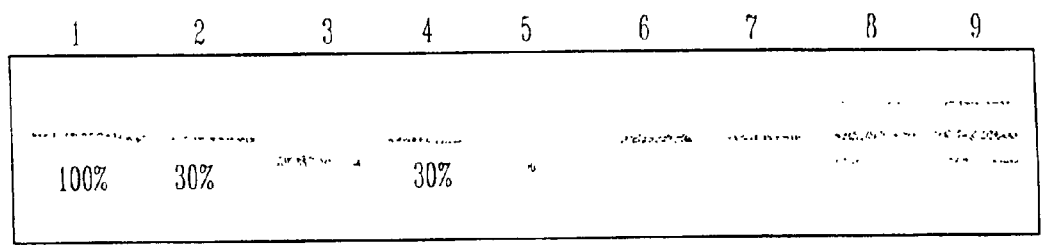

FIG. 12 is a Western blot analysis of corn kernels before and after extraction. Lanes: 1) before extraction; 2) after extraction at pH 7.5 without ME and SDS; 3) after extraction at pH 7.5 with ME and SDS; 4) after extraction at pH 10.0 without ME and SDS; 5) after extraction at pH 10.0 with ME and SDS; 6, 7, 8, 9) 0.05, 0.01, 0.1 and 0.2 µg GUS.

FIG. 13A–C sets forth the nucleotide SEQ ID NO: 4 and amino acid sequences of a gene cloned from *Trametes versicolor*.

Figure 14:
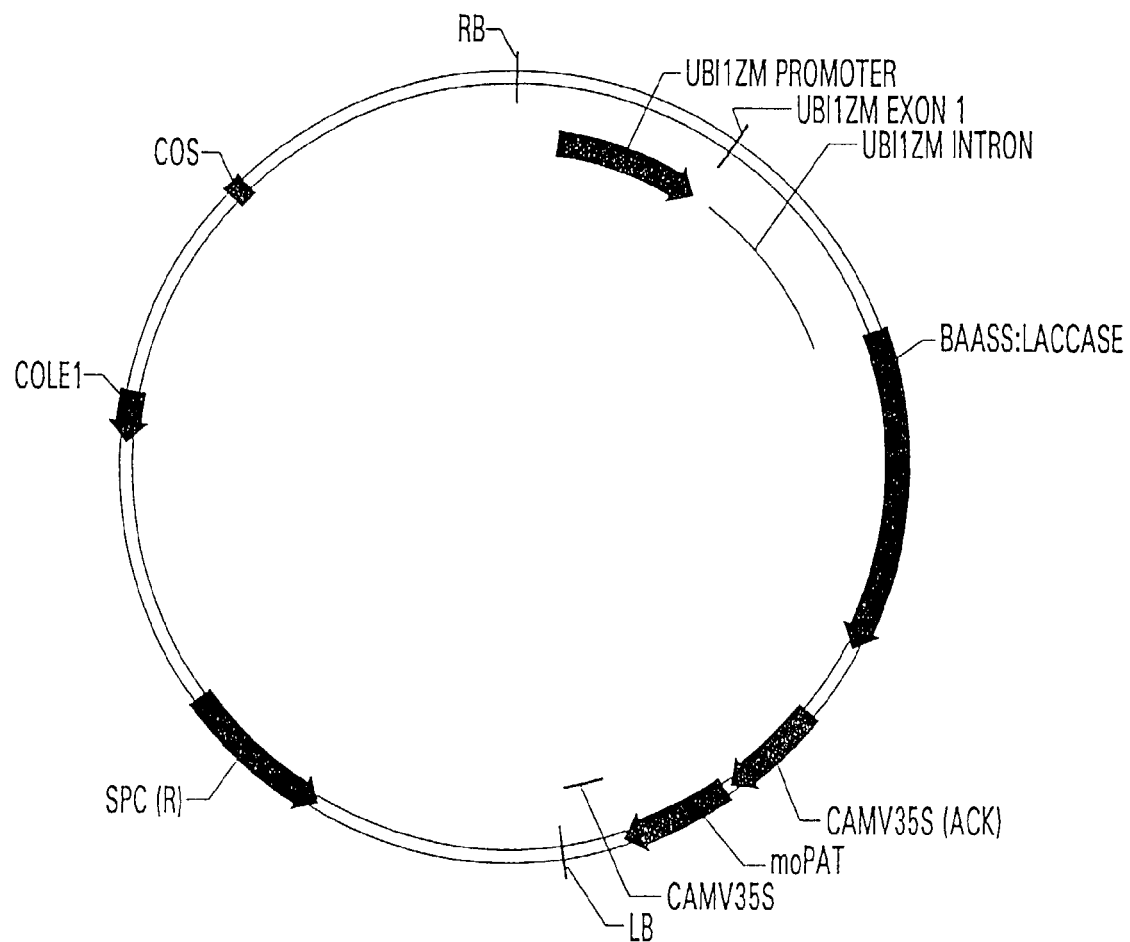

FIG. 14 shows p7718, a construct containing the laccase gene driven by the ubiquitin promoter, containing the barley alpha amylase sequence and the maize optimized PAT gene as a selectable marker, driven by 35S promoter. It further contains left and right borders of the t-DNA sequences.

Figure 15:
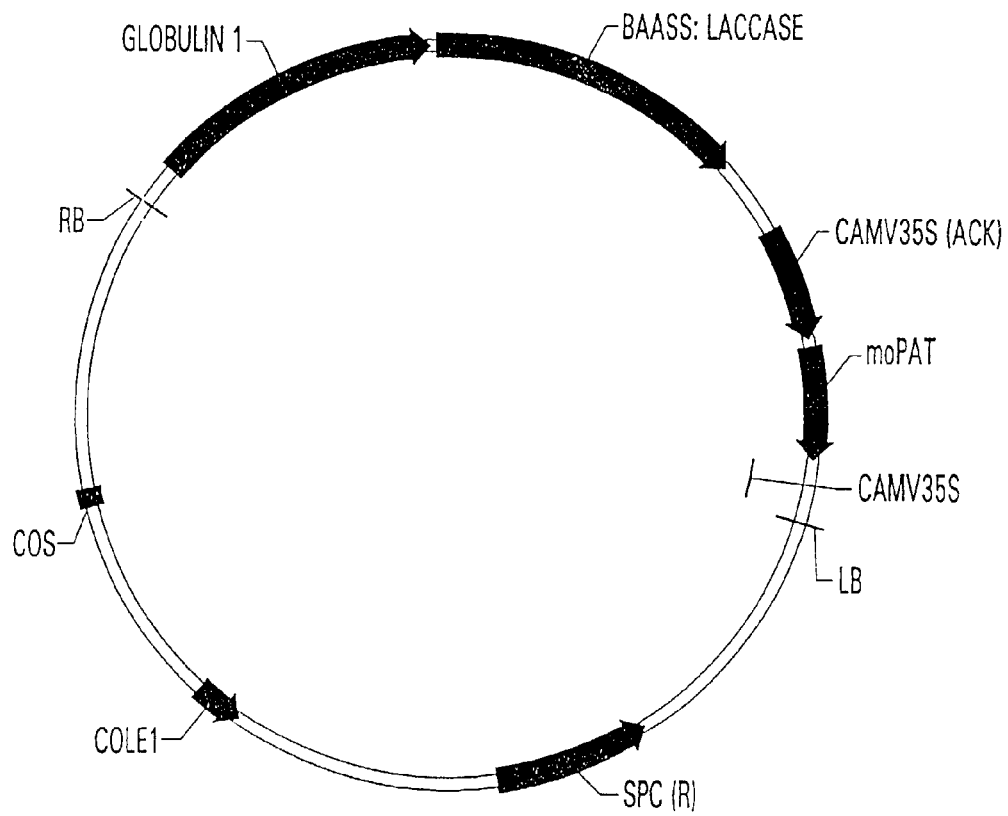

FIG. 15 shows pPGN8908, which is the same as 7718, except it substitutes the globulin promoter for the ubiquitin promoter.

Figure 16:
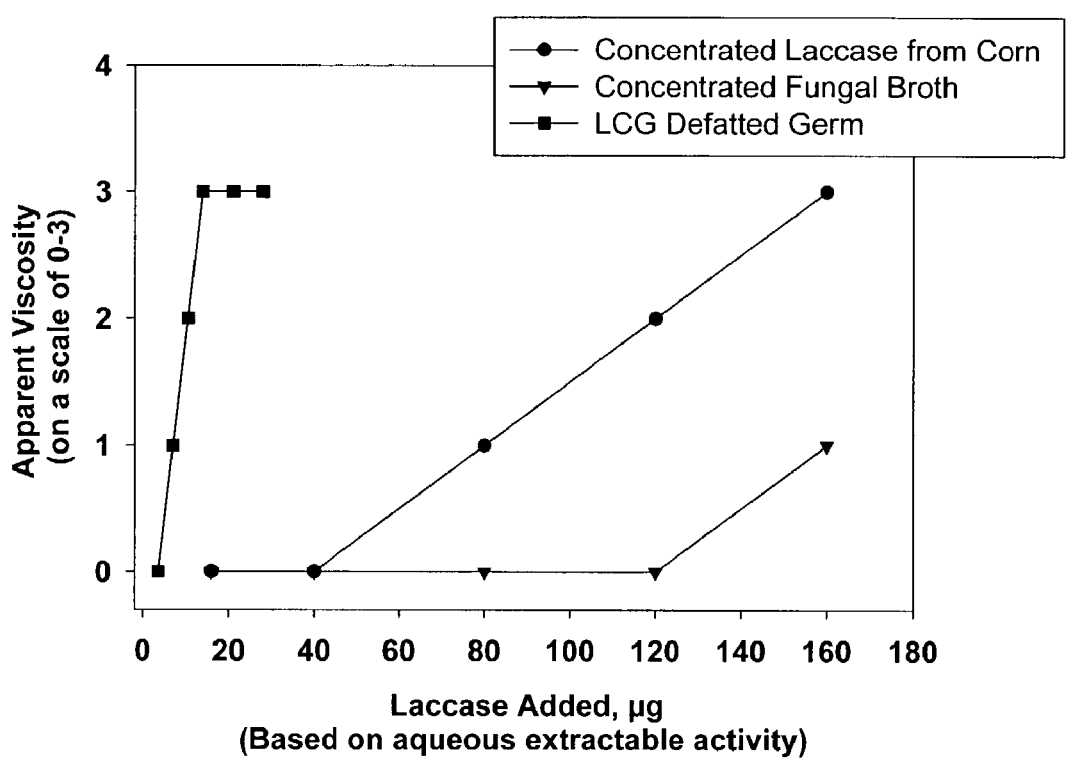

FIG. 16 is a graph showing qualitative viscosity analysis of bio-glue formation in the presence of laccase from different sources.

Figure 17:
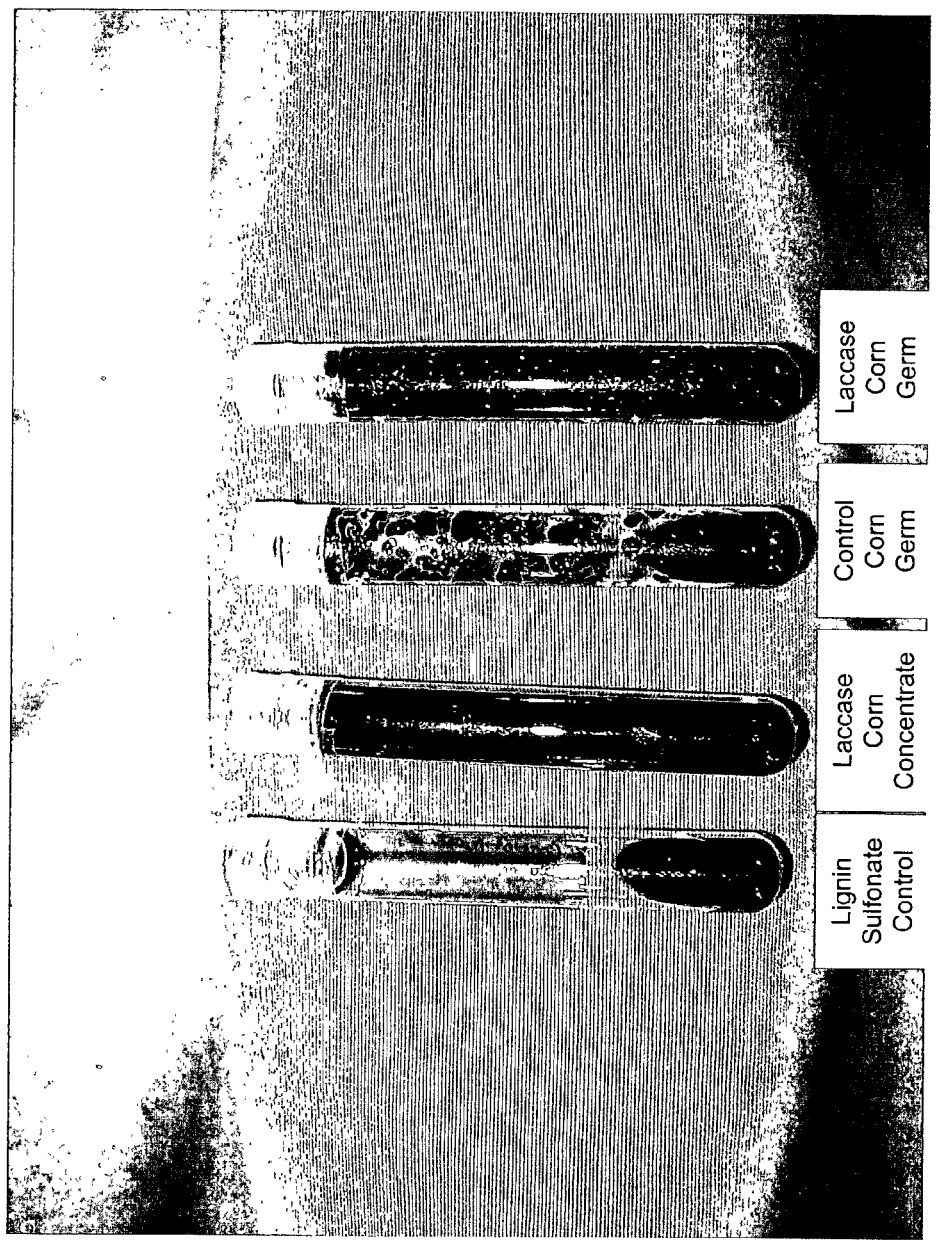

FIG. 17 is a photograph of laccase gelling of lignin sulfate.

DESCRIPTION OF THE SPECIFIC EMBODIMENTS

The inventors have determined that when heterologous genes are introduced into a plant for expression of a protein of interest, the germ portion of the seed may be separated from the remaining portions of the seed, with high levels of protein obtained and higher concentration is achieved on a dry weight basis compared to other portions of the seed or other plant tissue. Surprisingly high activity of the recombinant protein is maintained. For example, as discussed below, in transgenic maize seeds, 80% of the total kernel weight is endosperm, yet it contained only 22% of the avidin activity found in whole kernels. The embryo contained at least 55% of the avidin protein found in whole dry seed. In another example, rGUS concentration was six to ten times greater in the germ extract than in the kernel extract. Since the germ represents 10% of the corn seed, only small amounts of material must be used in downstream extraction and processing of the protein and in that 10% there is considerably more enrichment of the protein than in the seed as a whole. Increased efficiency in processing is thus achieved. Further, the 90% of the seed remaining can be used as a normal corn product for feed, food, or other commercial processes, thus resulting in additional revenues in the commercial protein production process.

Direction of expression of the protein to the germ is preferred according to the invention. It has been further determined by the inventors that the ubiquitin promoter directs expression preferentially to the germ of the seed. The example below demonstrates the ubiquitin promoter induced 10 to 20 fold higher levels of expression of the desired protein in seed as compared with other seed specific promoters.

In one embodiment of the invention, a gene encoding the protein of interest was linked to the ubiquitin promoter in a plasmid and plant material transformed by any one of numerous methods known to those skilled in the art for introducing heterologous genes into plant tissue. The plant tissue containing the gene was selected, cultured and grown, and seed harvested. The seed is dehulled and degermed, then air dried to about 15% moisture. It is then fractioned through a series of sieves and select fractions containing the majority of the germ aspirated at higher air velocity to obtain a germ-rich fraction. The germ was defatted with hexane and protein was extracted and air dried. Purification of the protein varies according to the protein being produced, and such methods are well known to those skilled in the art.

The plant germ when used in such commercial production must, naturally, be capable of being separated from the seed (degerminated) in a commercial milling process. One skilled in the art would readily appreciate that in plants such as tobacco seeds and many dicotyledons, the endosperm is absorbed into the cotyledons, and the embryo and endosperm cannot be degerminated in a commercial milling process. This is impractical in a commercial process. Monocotyledons, on the other hand, are the type of plant with an embryo that can be separated from the remainder of the seed in a commercial milling process. Therefore, it is those plants capable of degermination in a commercial milling process which fall within this invention. In a preferred method, corn germ is used as the source of the heterologous protein.

In another embodiment of the invention, a gene encoding the enzyme laccase is introduced into the plant and the germ used as the source of laccase in commercial processes. Until now, one skilled in the art was encouraged to extract the laccase from the plant tissue, and use it in commercial processes requiring laccase. The belief was that introduction of any extraneous material other than the protein to the process would unnecessarily add components to the mixture, and might hamper the process. Instead, the inventors here have discovered that it is not possible to completely extract laccase from the plant tissue. Unlike other enzymes produced in plants, the protein seems to adhere to the plant cell and is impossible to completely extract, even after numerous repeated extractions. Even after six extractions as much as 50% or more of the laccase protein remained bound to the plant cell. Thus, direct use of the germ plant tissue in this instance even further enhances the amount of protein which can be used in the process. By not extracting, and instead placing the germ tissue in the commercial process, it has been found that more of the laccase in that tissue is available. In addition, the laccase catalyzes the reaction without the addition of any other mediating substrates (such as ABTS).

The enzyme can be used in a number of different industrial processes. In one embodiment of the invention, plant germ containing laccase can be used in fiberboard production. In this method conglutination of wood fragments containing lignin occurs in an incubation mixture containing laccase in plant germ, thereby activating the lignin. See e.g. U.S. Pat. No. 5,618,482. Laccase can also substitute for less desirable adhesive resin solids to bond glued wood products. See, e.g. *Adhesives Ages*, supra. Its use as an adhesive includes construction and industrial plywood, oriented strand board, particleboard used for interior applications and medium density fiberboard. In another example, laccase can be used for an in-situ depolymerization of lignin in Kraft pulp, thereby producing a pulp with lower lignin content and lighter color. Such methods are described, for example, at Jim et al. (1991) *Holzforschung* (45(6): 467–468; U.S. Pat. No. 4,432,921. This use of laccase is an improvement over the current use of chlorine for depolymerization of lignin, which leads to the production of chlorinated aromatic compounds, which are an environmentally undesirable by-product of paper mills. Such uses are described in, for example, Martinez, A. T. et al., (1992)*J. Biotechnol.* 25:333–339; Hiroi et al. (1976) *Svensk papperstidning* 5:162–166. These are a few of the many uses to which the enzyme may be put.

In accordance with the present invention, a DNA molecule comprising a transformation/expression vector is engineered to incorporate protein-encoding DNA. Laccase is one of the examples shown below. Expression of laccase in plants is described at WO 2000/20625. Genes encoding this enzyme are well known. See for example U.S. Pat. No. 6,168,936. Some examples include the gene of laccase I cloned from *Aspergillus nidulans* as reported in Aramayo and Timberlake, *Nucleic Acids Res.* 18:3415 (1990); a laccase gene from *Phlebia radiata* and *Trichoderma reesei* described by Salohemo and Nicku-Paavola, supra; a gene from *Myceliophthora termophila* is discussed by Berka et al, supra and expressed in another fungus; a laccase gene from eucalyptus and pine for use in controlling lignin content in the plants is described in PCT/NS97/00112; a laccase-encoding tobacco gene is shown to also be used in controlling lignin content of the transformed plant at WO 97/45549; a laccase-encoding gene corresponding to a *Rhizoctonia solani* gene is set forth in 5,480,801 and expressed in a microbe; and a gene from a basidiomycete, *Polyporus pinsitus* is discussed in U.S. Pat. No. 5,667,531, also expressed in a transformed microbe. The gene used in the present invention is from *Trametes versicolor* (See Example 4). A gene for use in the present invention can be subcloned in a vector of choice.

In another example of DNA isolation, it is possible to screen a cDNA library with anti-laccase antibodies. The known methodologies used would include identification of the gene by hybridization with probes, PCR, probe/promoter/synthetic gene synthesis, sequencing, molecular cloning and other techniques which are well known to those skilled in molecular biology. While it is possible to synthesize the gene to reflect preferred codon usage in plants, and may be useful in increasing expression of laccases, (See, Murray et al, *Nucleic Acid Res.* 17:477–498 (1980)), it may not be necessary in all cases, as was found with the gene used in the examples below. In addition to the exemplified laccase DNA and proteins taught herein, the present invention contemplates any laccase producing gene.

In a preferred embodiment of the invention, expression of the protein in the plant may be increased by directing expression to the cell wall. This may be accomplished by use of a signal sequence and in a preferred embodiment is the barley alpha amylase signal sequence, Rogers, *J. Biol. Chem.* 260:3731–3738 (1985), or brazil nut protein signal sequence when used in canola or other dicot. Another alternative is to express the enzyme in the endoplasmic reticulum of the plant cell. This may be accomplished by use of a localization sequence, such as KDEL SEQ ID NO: 1. This sequence contains the binding site for a receptor in the endoplasmic reticulum. Munro, S. and Pelham, H. R. B. 1987 "A C-terminal signal prevents secretion of luminal ER proteins." *Cell.* 48:899–907. The use of such a localization sequence will increase expression over levels obtained when the enzyme is otherwise expressed in the cytoplasm.

The methods available for putting together such a relatively short synthetic gene comprising the various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene has been isolated and engineered to contain some or all of the features described above, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the laccase; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker which is functionally linked to a promoter that controls transcription initiation. For a general description of plant expression vectors and reporter genes, see Gruber et al, "Vectors for Plant Transformation" in *Methods of Plant Molecular Biology and Biotechnology* 89–119 (CRC Press, 1993).

Promoter elements employed to control expression of the protein and the selection gene, respectively, can be any plant-compatible promoter. Those can be plant gene promoters, such as, for example, the ubiquitin promoter, the promoter for the small subunit of ribulose-1, 5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al, *Science* 236:1299 (1987) and European patent application No. 0 342 926. See international application WO 91/19806 for a review of illustrative plant promoters suitably employed in the present invention. The range of available plant compatible promoters includes tissue specific and inducible promoters. In one embodiment of the present invention, the exogenous DNA is under the transcriptional control of a plant ubiquitin promoter. Plant ubiquitin promoters are well known in the art, as evidenced by European patent application no. 0 342 926.

In a further preferred embodiment, a tissue specific promoter is provided to direct transcription of the DNA preferentially to the seed. One such promoter is the globulin promoter. This is the promoter of the maize globulin-1 gene, described by Belanger, F. C. and Kriz, A. L. at "Molecular Basis for Allelic Polymorphism of the Maize Globulin-1 gene" *Genetics* 129:863–972 (1991). It also can be found as accession number L22344 in the Genbank database. Another example is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" *The Plant Cell* Vol. 1, 839–853 (1989).

In another preferred embodiment, the selective gene is a glufosinate-resistance encoding DNA and in a preferred embodiment can be the phosphinothricin acetyl transferase ("PAT") or maize optimized PAT gene under the control of the CaMV 35S promoter. The gene confers resistance to bialaphos. See, U.S. Pat. No. 6,096,947; Gordon-Kamm et al, *The Plant Cell* 2:603 (1990); Uchimiya et al, *Bio/Technology* 11:835 (1993), and Anzai et al, *Mol. Gen. Gen.* 219:492 (1989).

Obviously, many variations on the promoters, selectable markers and other components of the construct are available to one skilled in the art.

In accordance with the present invention, a transgenic plant is produced that contains a DNA molecule, comprised of elements as described above, integrated into its genome so that the plant expresses a heterologous laccase-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al, "Procedures for Introducing Foreign DNA into Plants" in *Methods in Plant Molecular Biology and Biotechnology*, Glick et al (eds) pp. 67–68 (CRC Press 1993) and by Phillips et al, "Cell/Tissue Culture and In Vitro Manipulation" in *Corn and Corn Improvement* 3d Edit. Sprague et al (eds) pp. 345–387 (American Soc. Of Agronomy 1988). The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al, *Bio/Technology* 10:268 (1992); and Weisinger et al., *Ann. Rev. Genet.* 22: 421–477 (1988). For example, the DNA construct may be introduced into the genomic DNA of the plant cell using techniques such as microprojectile-mediated delivery, Klein et al., *Nature* 327: 70–73 (1987); electroporation, Fromm et al., *Proc. Natl. Acad. Sci.* 82: 5824 (1985); polyethylene glycol (PEG) precipitation, Paszkowski et al., *Embo J* 3: 2717–2722 (1984); direct gene transfer, WO 85/01856 and EP No. 0 275 069; in vitro protoplast transformation, U.S. Pat. No. 4,684,611; and microinjection of plant cell protoplasts or embryogenic callus. Crossway, *Mol. Gen. Genetics* 202:179–185 (1985). Co-cultivation of plant tissue with *Agrobacterium tumefaciens* is another option, where the DNA constructs are placed into a binary vector system. Ishida et al., "High Efficiency Transformation of Maize (Zea mays L.) Mediated by *Agrobacterium tumefaciens*" *Nature Biotechnology* 14:745–750 (1996). The virulence functions of the *Agrobacterium tumefaciens* host will direct the insertion of the construct into the plant cell DNA when the cell is infected by the bacteria. See, for example Horsch et al., *Science* 233: 496–498 (1984), and Fraley et al., *Proc. Natl. Acad. Sci.* 80: 4803 (1983).

Standard methods for transformation of canola are described by Moloney et al. "High Efficiency Transformation of *Brassica napus* Using *Agrobacterium* Vectors" *Plant Cell Reports* 8:238–242 (1989). Corn transformation is described by Fromm et al, *Bio/Technology* 8:833 (1990) and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al., "Efficient Transformation of Rice (Oryza sativas L.) Mediated by *Agrobacterium* and Sequence Analysis of the Boundaries of the T-DNA" *The Plant Journal* 6(2): 271–282 (1994), Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. Sorghum transformation is described by Casas et al, supra and by Wan et al, *Plant Physiolog.*

104:37 (1994). Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* specific replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing a fresh culture of the *Agrobacterium* on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. "Establishment and maintenance of friable, embryogenic maize callus and involvement of L-proline" Planta (1985) 154:207–214. The resuspension medium is the same as that described above. All further Hi II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of protein, and it is thus useful to ascertain expression levels in transformed plant cells, transgenic plants and tissue specific expression. One such method is an ELISA assay which is well known to one skilled in the art. The ELISA assay used for measuring laccase expression uses biotinylated anti-laccase polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection.

The levels of expression of the gene of interest can be enhanced by the stable maintenance of a protein encoding gene on a chromosome of the transgenic plant. Use of linked genes, with herbicide resistance in physical proximity to the laccase gene, would allow for maintaining selective pressure on the transgenic plant population and for those plants where the genes of interest are not lost.

With transgenic plants according to the present invention, proteins can be produced in commercial quantities. Thus, the selection and propagation techniques described above yield a plurality of transgenic plants which are harvested in a conventional manner. Germ from the plant with the protein of interest can be used in the processing. When using the plant germ itself, it can, for example, be added intact, can be powdered and then applied in the commercial process, or made into flour.

The laccase gene may also be included in a plant that contains one of the mediators that is useful in commercial application of laccase. Laccase is a large molecule, and hence when used in such processes as delignification, may be enhanced by the use of a mediator. It was found that fungi that degrade wood secrete low molecular weight compounds which act to allow penetration of the wood fibers. Mediators include 1-hydroxybenzotriazole (HBT), 2,2' azeno-bis-(3-ethylbenzothiazoline-6-sulfonic acid) (ABTS), 1-nitroso-2-naphthol-3,6-disulfonic acid (NNS) and chlorpromazine (CPZ), to name a few. One review of such mediators is found at M. Amann, "The Lignozyme Process-Coming Closer to the Mill" *International Symposium on Wood and Pulping Chemistry* $9^{th}$, Montreal, Technical Section, Canadian Pulp and Paper Association. Classes of enhancers are also described in WO 94/12619, WO 94/12620, WO 94/12621 and WO 98/23716. An overview of laccase and mediators is provided at H. P. Call, I. Mucke, *Journal of Biotechnology* (1997) 53:163–202.

It is believed that corn may be providing its own mediator, but it may be desirable in some instances to add a mediator. Any method to combine the gene with the plant having the mediator will meet the goal, and the process used will vary depending upon the resources of the manufacturer, and the plants involved. By way of example, the laccase gene may be introduced directly into the plant, or a plant with the laccase gene may be backcrossed into the plant having the mediator substance. Backcrossing is a method in which a desirable trait is transferred from one plant into another plant which lacks the trait, but contains other desirable characteristics. By use of a selectable marker, presence of the laccase gene may be confirmed. The progeny is then crossed again to a plant having the mediator. This plant may be then used for generation of laccase and the mediator within the resulting plant, or further backcrossing may be used so that the resulting plant is like the mediator-containing plant in all aspects except that it contains the laccase gene.

The following is provided by way of example and is not intended to limit the scope of the invention. Those skilled in the art will appreciate that variations in the procedures and materials described are possible and yet still fall within the scope of the invention.

EXAMPLE 1

Commercial Production of Avidin in Germ

Avidin has been produced in transgenic maize seed. See U.S. Pat. No. 5,767,379. The glycoprotein is native to avian, reptilian, and amphibian egg white. Transcription of the heterologous gene was driven by the maize ubiquitin promoter, and translation was targeted to the endoplasmic reticulum surface because of an attached signal sequence. A transformant showing high-level expression of avidin was selected. Southern blot data revealed that four copies of the gene are present in this transform ant. The foreign protein represents >2% of aqueous soluble extracted protein from populations of dry seed, a level higher than any heterologous protein previously reported for maize. In seed, greater than 55% of the extractable transgenic protein is present in the embryo, an organ representing only 12% of the dry weight of the seed. This indicates that the ubiquitin promoter previously considered to be constitutive, in this case shows a strong tissue preference in the seed, and further to the germ of the seed. Subcellular localization of the mature protein is primarily localized to the intercellular spaces.

For production, transgenic maize plants were grown in isolation plots up to one half acre in size. An interesting trait of the transgenic plants expressing avidin is that the presence of the gene correlates with partial or total male sterility. Because of this trait, no homozygous plants have been obtained. Seed populations from transgenic plants were maintained by outcrossing and segregate 1:1 for the trait. In generations T2–T4, avidin expression remained high at 2.3% (230 mg/kg seed) of extractable protein from seed, though it varied from 1.5–3.0%. However, levels of expression did not appear to depend on pollen parent or growing location. Production fields of this male sterile line yielded approximately 230 mg avidin protein per kg of seed. Processing steps of harvested seed that included drying ears to 13% moisture at up to 40° C., shelling ears for seed storage, and cracking and flaking kernels prior to protein extraction generated no apparent loss of avidin activity. Some seed was dry milled to enrich for embryos, the fraction which contained most of the avidin, to test the efficacy of embryo enrichment in large scale purification applications. Cracked and flaked kernels stored at −29° C. or 10° C. for up to three months showed no significant loss of avidin activity. Commercial processing steps of harvested seed also generated no apparent loss of activity. Storage at higher temperatures lowered activity after one to three weeks. Avidin activity in maize seed extracts showed no significant susceptibility to endogenous protease activity. The protein was purified to greater than 90% purity by affinity chromatography after extraction from mature maize seed. Physical characterization of purified maize-derived avidin demonstrated that the N-terminal amino acid sequence and biotin binding characteristics are identical to the native protein with near identical molecular weight and glycosylation.

Avidin is a glycoprotein found in avian, reptilian and amphibian egg white. Its gene expression is induced by progesterone as well as by certain events, such as tissue trauma, the presence of toxic agents, and bacterial and viral infections. Induction appears to be primarily at the transcriptional level. The protein avidin is composed of four identical subunits, each 128 amino acids long, the amino acid sequence of which has been known since 1971 [DeLange R J, Huang T S: Egg White Avidin III. Sequence of the 75-residue middle cyanogen bromide peptide. Complete amino acid sequence of the protein subunit. J. Biol. Chem. 246: 698–709 (1971).]. The cDNA of the chicken oviduct avidin gene was documented by Gope et al. [Gope M L, Keinanen R A, Kristo P A, Conneely O M, Beattie W G, Zarucki-Schulz T, O'Malley B W, Kulomaa M S: Molecular cloning of the chicken avidin cDNA. Nuc. Acids Res. 15: 3595–3606 (1987).] and a genomic lone was isolated Keinanen et al. [Keinanen RA, Laukkanen M-L, Kulomaa M S: Molecular cloning of three structurally related genes for chicken avidin. J. Steroid Biochem. 30: 17–21 (1988)]. Keinanen et al. [Keinanen R A, Wallen M J, Kristo P A, Laukkanen M O, Toimela T A, Helenius M A, Kulomaa M S: Molecular cloning and nucleotide sequence of chicken avidin-related genes 1–5. Eur. J. Biochem. 220: 615–21 (1994).] reported on a family of closely related avidin genes from chicken.

Avidin forms a particularly strong, non-covalent bond with biotin. It is this property of avidin that is responsible for its commercial value, because it allows for detection of protein and nucleic acid molecules that have biotin incorporated into their structure. The customary source for commercial production of avidin has been chicken egg white, a method of relatively high production costs. (Abbreviations: HABA, 4-hydroxyazobenzene-2'-carboxylic acid; 2-ME, beta mercaptoethanol; EDTA, ethylenediamine tetraacetic acid; PMSF, phenylmethanesufonyl fluoride; PBS, phosphate buffered saline; SDS-Page, sodium dodecy sulfate polyacrylamide gel electrophoresis; TBST, Tris buffered saline Tween; BSA, bovine serum albumin; ECI, enhanced chemiluminescence: pNPP, para nitrophenyl phosphate.)

Materials and Methods

Construction of Plasmids Used for Transformation.

Figure 1A:
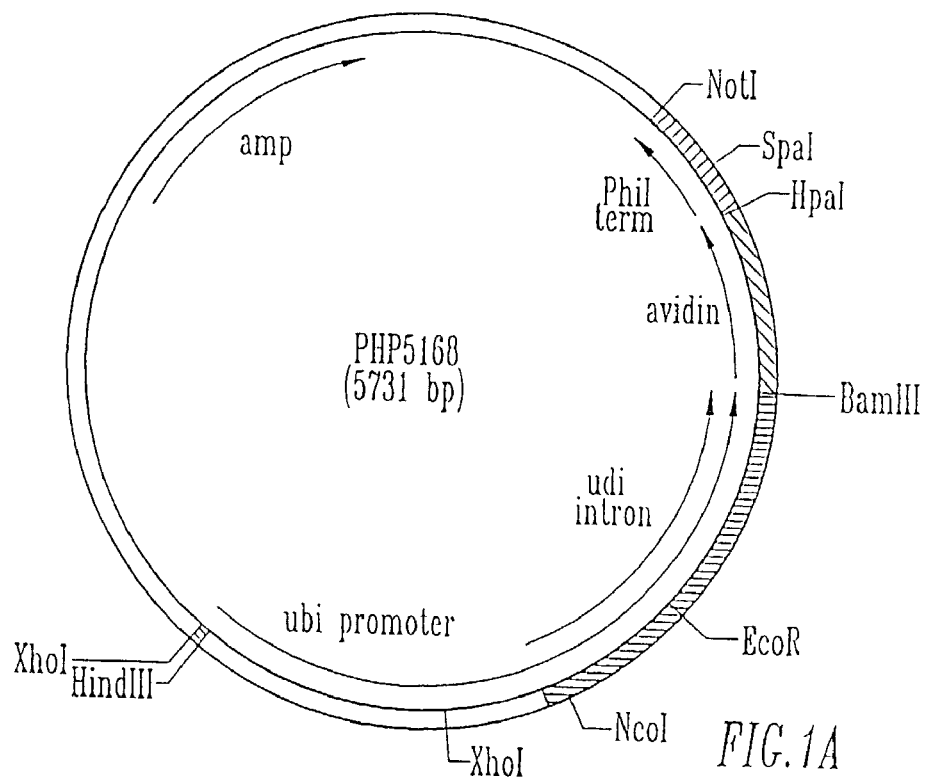
FIG. 1: Restriction endonuclease maps of plasmids used for maize transformation to generate the avidin-1 line. A. PHP5168 is composed of a maize ubiquitin promoter and nontranslated first exon with intron, a barley alpha amylase signal sequence, (BAASS) a gene encoding chicken avidin and the PinIII terminator cloned into a Bluescript SK+ plasmid backbone. B. PHP610 is composed of the tandem CaMV promoter followed by the AdH1 intron from maize, the bar gene and the PinII terminator cloned into Bluescript SK+. amp=resistance to ampicillin.

The chicken egg white avidin cDNA was reported by Gope et al. supra. The amino acid sequence was reverse translated into nucleic acid sequence utilizing a preferred maize codon usage table (GCG, assembled by Mike Cherry, Stanford University). From this computer-generated synthetic sequence, overlapping, complementary oligonucleotides with compatible restriction site termini were designed, then annealed and ligated to yield the maize optimized gene. The barley alpha amylase signal sequence [Rogers J C: Two barley alpha-amylase gene families are regulated differently in aleurone cells. J. Biol. Chem. 260: 3731–3738 (1985).] was also synthesized (using overlapping, complementary nucleotides) with maize-preferred codons. Compatible restriction sites between these two gene fragments were ligated, with the signal sequence at the 5' end of the avidin gene. The resultant signal sequence/avidin segment was cloned, as a BamHI/EcoRI fragment, into the vector pGEM3Zf+, a product of Promega Corporation (Madison, Wis.), to generate plasmid PHP5142. A BamHI/HpaI fragment containing the signal sequence/avidin region was isolated and cloned into a plasmid (PHP5038) derived from pBlueScript SK+, as a backbone (Stratagene, La Jolla, Calif.). In this plasmid, the signal sequence/avidin gene fragment was inserted between the maize ubiquitin 5' region, which includes the promoter, the first exon and first intron [Callis J, Fromm M, Walbot V: Introns increase gene expression in cultured maize cells. Genes and Development 1: 1183–1200 (1987), Cornejo M, Luth D, Blankenship K, Anderson O, Blechl A: Activity of a maize ubiquitin promoter in transgenic rice. Plant Mol. Biol. 23:567–581 (1993), European Patent # 0 342 926], and the potato proteinase inhibitor II (PinII) transcription terminator region [An G, Mitra A, Choi H K, Costa M A, An K, Thornburg R W, Ryan C A:. Functional analysis of the 3' control region of the potato wound-inducible proteinase inhibitor II gene. Plant Cell 1:115–122 (1989)]. The resultant plasmid is PHP5168 (FIG. 1A).

Figure 1B:
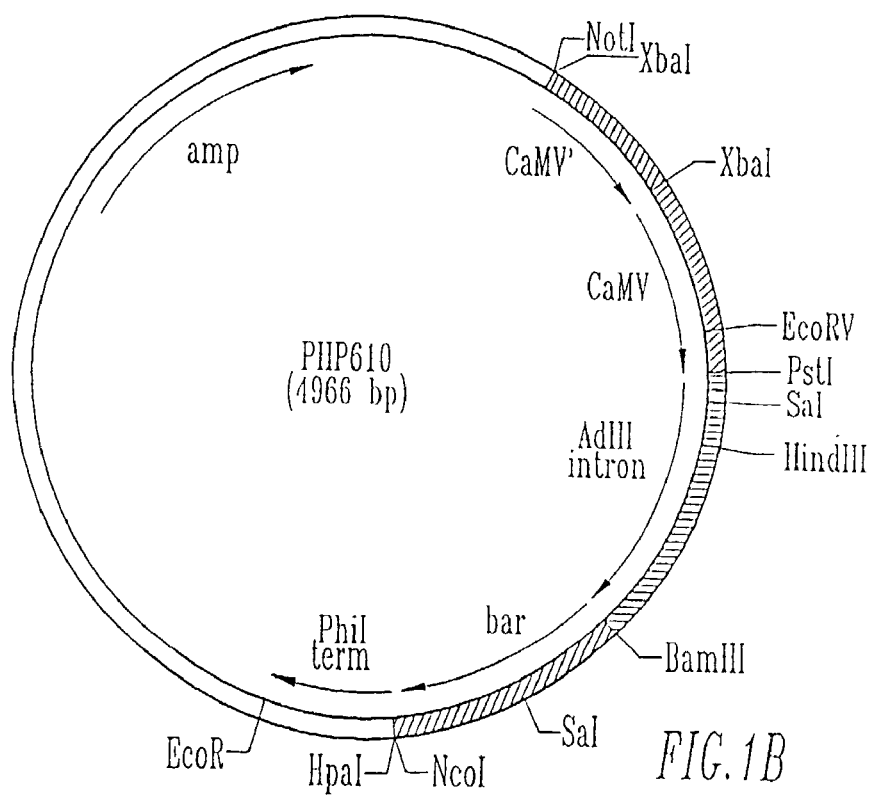

The 560 base pair coding sequence of the bar gene from *Streptomyces hygroscopicus* was removed as a PvuII/HincII fragment and ligated into a Bluescript SK+-based plasmid (PHP289). This plasmid contained from previous cloning steps the double 35S promoter [Nagy F, Odell J T, Morelli G, Chua N H: Properties of expression of the 35S promoter from CaMV in transgenic tobacco plants. Biotechnology in plant science: relevance to agriculture in the eighties. Milton Zaitlin, Peter Day, and Alexander Hollaender, eds. Academic Press, Orlando, Fla. p. 227–235 (1985)], the Tobacco Mosaic Virus omeg' leader [Gallie D R, Sleat D E, Watts J W, Turner P C, Wilson T M A: The 5'-leader sequence of tobacco mosaic virus RNA enhances the expression of foreign gene transcripts in vitro and in vivo. Nuc. Acids Res. 15:3257–3273 (1987), the intron from the maize alcohol dehydrogenase gene [Callis, supra] and the potato pinII terminator [An, supra] The resultant expression cassette for herbicide resistance is plasmid PHP610 (FIG. 1B)

Transformation and Tissue Culture.

An established callus line derived from a single immature embryo of the Hi-II maize germplasm was transformed using particle bombardment-mediated transformation with helium-powered particle acceleration device, PDS 1000 (Bio-Rad, Hercules, Calif.). Tissue showing a friable type-II embryogenic morphology was sieved through 710 μm mesh prior to co-transformation with equimolar amounts of the avidin gene (PHP5168) and the bar selectable marker gene (PHP610), according to the procedures of Tomes, D. Ross M C, Songstad D D: Direct DNA transfer into intact plant cells via microprojectile bombardment. O L Gamborg and G C Phillips, eds., Plant Cell Tissue and Organ Culture: Fundamental Methods. Springer-Verlag, Berlin, Heidelberg. pp.197–213 (1995). Transformants expressing the bar gene were selected in the presence of bialaphos (3mg $1^{-1}$), according to the protocol of Register et al. [Hancock K, Tsang VCW: India ink staining of protein on nitrocellulose paper. Anal. Biochem. 133:157–162 (1983)]. Co-transformants that also expressed the avidin gene were identified by ELISA screening of the selected colonies. Multiple plants ($T_0$ generation) were regenerated from avidin-expressing colonies, transferred to the greenhouse and assayed for avidin expression in leaf tissue. $T_1$ seed was obtained by outcrossing, with the $T_0$ plants as the female parent and a non-transformed inbred line (PHN46) as the male parent.

Light Microscopy

Light microscopy was performed on embryo pieces fixed overnight in 0.5% glutaraldehyde/3% paraformaldehyde in 0.01 M sodium phosphate buffer pH7.2, dehydrated in an ethanol series and embedded in LR White acrylic resin (EM Sciences, Fort Washington, Pa.). Sections 1–2 microns) were cut on a Reichert Ultracut S ultramicrotome. Slides were blocked with 2% powdered milk and 1% BSA plus 1% normal goat serum (NGS) in Tris buffered saline with Tween-20 (TBST; 0.01 M Tris, pH 8.0; 0.15 M sodium chloride; 0.05% Tween-20) overnight, incubated at room temperature for 1 hour with primary antibody (anti-avidin serum antibody, ICN) diluted 1:100 in blocking buffer, washed 3×10 minutes in TBST, incubated at room temperature for 1 hour with secondary antibody (goat anti-rabbit TRITC conjugate, Sigma Chemical Co.) diluted 1:100 in blocking buffer, washed 3×5 min in TBST, 2×1 minute in water. Slides were viewed with phase contrast or epifluorescence on a Leica DMRB microscope and photographed on Fujichrome 1600 slide film. Images were scanned using Photoshop (Adobe) software and labeled with Freehand (Macromind) software.

Tissue Printing

Tissue prints of developing kernels (approximately 40 days after pollination, DAP, [Fritz S E, Hood K R, Hood E E: Localization of soluble and insoluble fractions of hydroxyproline-rich glycoproteins during maize ]) were made on nitrocellulose that had been wet with distilled water and air dried. Prints were either stained with India Ink or reacted with anti-avidin polyclonal antibodies (ICN) diluted 1:1000 in TBST. Secondary antibodies (Sigma Chemical Co.) were goat anti-rabbit IgG conjugated to alkaline phosphatase and were diluted 1:1000 in TBST. Negative controls consisted of either no primary antibodies or maize of the same genotype transformed with a different gene. Incubation conditions were as described by Fritz et al. supra. Images were scanned and labeled as above.

Southern Blotting

High molecular weight genomic DNA was isolated from lyophilized young maize leaves from which the mid-vein had been removed. Digested DNA (10 μg per lane) was electrophoresed in 0.8% agarose gels and transferred to Hybond-N nylon membranes (Amersham) and hybridized as described by Lowe et al. [Lowe K, Bowen B, Hoerster G, Ross M, Bond D, Pierce D, Gordon-Kamm B: Germline transformation of maize following manipulation of chimeric shoot meristems. Bio/Technology 13:677–682 (1995]. $^{32}$P-labeled probes were prepared using a Rediprime kit (Amersham). The avidin probe was a 470 base pair fragment of the avidin gene from the plasmid shown in FIG. 1A. The phosphinothricin resistance gene was probed with a 567 base pair fragment of the bar gene as shown in plasmid PHP610 in FIG. 1B. Hybridization was detected on Amersham Hyperfilm using two screens. Exposure times varied with the intensity of the signal on the blot, but typically overnight.

PCR

DNA was isolated from leaf tissue pieces the size of a small paper punch using the method of Jhingan. [Jhingan A K: A novel technology for DNA isolation. Methods Mol. Cell. Biol. 3:15–22 (1992)] DNAs were resuspended in a small volume of Tris:EDTA (pH 8.0) in a 10 mM, 1 mM ratio. Prior to PCR, the DNA samples were heated at 65° C. for 10 min. All PCR reactions were performed with a 25 μl volume in 96 well plates and contained 2 μl isolated DNA, 240 μM dNTPs (Pharmacia), 1 unit Taq polymerase (Boehringer Mannheim Biochemicals, BMB, Indianapolis, Ind.), and 1× reaction buffer (BMB). Oligonucleotide primers (1 μM each), 20 base pairs in length, that corresponded to sequences in the avidin gene, amplified a DNA fragment approximately 450 base pairs in size. Amplification was achieved using an initial melting step at 94° C. for 1.5 min., then 35 cycles of 94° C. for 40 seconds, annealing at 62° C. for 60 seconds, and lengthening at 72° C. for 1 minute in a Biotherm oven.

Scoring of Male Sterility

When ear shoots on plants in the field began to show silk, the tassels were examined for extrusion of anthers. Plants that showed no anther extrusion were scored as completely sterile. Plants with extrusion of a few anthers that contained no pollen were scored as shedders or partially sterile plants. Plants were observed two days after the initial scoring to confirm the phenotype.

Biochemical Materials

The ECL (Enhanced Chemiluminescence) kit was purchased from Amersham (Arlington Heights, Ill.). The 2-iminobiotin agarose resin and 4-hydroxyazobenzene-2'-carboxylic acid (HABA) were obtained from Sigma Chemical Co. (St. Louis, Mo.). The rabbit polyclonal antibodies raised against avidin were obtained from ICN (Costa Mesa, Calif.). Horseradish peroxidase-conjugated secondary antibodies were from BMB. N-Glycosidase A was purchased from Seikagaku America (Ijamsville, Md.). All other chemicals were of reagent grade.

ELISA for Quantitation of Avidin

ELISAs were conducted on extracts of leaves or seed. Samples were ground in a mortar and pestle (leaves) or a coffee grinder (seeds) and extracted in 50 mM PBS pH 7.0 containing 0.05% Tween-20. Total protein was quantified using the Bradford assay [Bradford M: A rapid and sensitive method for the quantification of microgram quantities of protein utilizing the principle of protein-dye binding. Anal. Biochem. 72:248–254 (1976)]. ELISAs were typical sandwich style in which the microtiter plates were coated with rabbit anti-avidin antibody (Vector Labs, Burlingame, Calif.), the avidin protein was captured overnight at 4° C., was reacted with biotinylated anti-avidin antibody (1 hour, 37° C.) then with Zymed streptavidin conjugated to alkaline phosphatase (1 hour, 37° C.). The alkaline phosphatase was detected with para nitrophenyl phosphate (pNPP) at 1 mg $ml^{-1}$ in 10% diethanolamine buffer at 37° C. Plates were read after 0.5 and 1 hour at 405 nm on a microplate reader, Spectra Max 250 using the Softmax Pro software (Molecular Devices, Sunnyvale, Calif.).

SDS-PAGE and Immunoblot Analysis.

Proteins were analyzed by SDS-PAGE using 4–20% gradient gels (Novex, San Diego, Calif.) and the buffer system of Laemmli [26]. Gels were stained with Coomassie blue or transferred to ImmpbilonP-PVDF (Millipore) for immunoblot analysis as previously described [Witcher D R, DeWaard M, Liu H, Pragnell M, Campbell K P: Association of native $Ca^{2+}$ channel B subunits with the a1 subunit interaction domain. J. Biol. Chem. 270:18088–18093 (1995]. Immunoblots were blocked for 1 h in TBST containing 5% nonfat dry milk (Blotto). Blots were incubated overnight in affinity-purified anti-avidin polyclonal antibodies at a dilution of 1:100. The blots were washed 3×10 minutes in TBST, then incubated for 1 hour in goat anti-rabbit secondary antibody conjugated to horseradish peroxidase at a dilution of 1:5000. After washing 3×10 min in TBST, the blots were developed using Amersham's enhanced chemiluminescence (ECL) protocol.

Affinity-urification of Anti-avidin Polyclonal Antibodies

Rabbit polyclonal antibodies were affinity purified [Sharp A H, Campbell K P: Characterization of the 1,4-dihydropyridine receptor using subunit-specific polyclonal antibodies: evidence for a 32,000 Da subunit. J. Biol. Chem. 264: 2816–2825 (1989)] using Immobilon-P transfer strips containing purified chicken egg white avidin (Sigma Chemical Co.). Briefly, Immobilon-P transfer strips with bound purified chicken avidin were incubated overnight with 100 µl of serum diluted in TBS. The strips were washed 3×10 minutes with 50 mM Tris (pH 7.4), 500 mM NaCl then washed 3×10 minutes with 50 mM Tris (pH 7.4), 150 mM NaCl. The polyclonal antibodies were eluted from the strips with 50 mM glycine (pH 2.5). The purified antibodies were neutralized with 1 M Tris (pH 8.0).

Deglycosylation of Avidin

Two µg of purified maize-derived avidin or native chicken avidin (Sigma Chemical Co.) were dissolved in a buffer containing 10 mM sodium acetate (pH 5.1), 0.375 M sodium isothiocyante, and 50 mM B-mercaptoethanol. N-glycosidase A (NGA) was added to a final concentration of 0.2 units $ml^{-1}$, and incubated at 37° C. for 18 to 24 hours. The reaction was stopped by boiling for 2 minutes in SDS-PAGE sample buffer, then analyzed by SDS-PAGE.

Biotin Inhibition of HABA Binding to Avidin

One hundred µg of purified maize-derived avidin or native chicken avidin were diluted to 1 ml with phosphate buffered saline (0.01 M $NaPO_4$ pH 7.0; 0.15 M NaCl, PBS) for the avidin activity assay. Twenty-five µl of 10 mM HABA (pH 7.6) [29] were added to the 1 ml of PBS containing avidin solution, and the solution read at 500 nm on a Beckman DU-640, a reading representing 0% inhibition. One µl of 0.125 mg $ml^{-1}$ biotin was then added to the solution, and after mixing thoroughly, read again at 500 nm, and repeated until no change was observed in the OD. The normalized absorbance value was obtained by subtracting from all the absorbance values, the value at which the absorbance change stopped. The 0% inhibition value was set to 1.0 and all the other absorbance values were scaled accordingly.

Separation of Maize Embryo (germ) and Endosperm

Five hundred grams of dry kernels (12% moisture) were placed in a polyethylene bag and moisture-conditioned at 4° C. to the preselected moisture content (MC) by adding water to 16% MC using a 16 hours holding time, increasing to 21% MC in an additional 1.5 hours, and to a final 24% MC in 15 minutes. After conditioning, the kernels were passed through a horizontal custom-made dehuller/degermer, which was operated at 16,000 rpm, at a feed rate of approximately 18 kg $h^{-1}$.

The dehulled and degermed seed was air-dried at room temperature to 15% moisture and fractionated through a series of sieves (Standard Testing Sieves, Fisher Scientific, Philadelphia, Pa.) (Table 1 and 2).

TABLE 1

Size of sieve openings and fraction of maize seed retained by the sieves.

| | Sieve number | | | | | | |
|---|---|---|---|---|---|---|---|
| | 5 | 7 | 12 | 25 | 50 | 100 | flow through |
| Sieve openings (mm) | 4.00 | 2.83 | 1.68 | 0.71 | 0.30 | 0.15 | <0.15 |
| Retained fraction (% of dry weight) | 2.5 | 9.7 | 20.8 | 31.6 | 18.5 | 16.4 | 0.5 |

TABLE 2

Schedule for increasing moisture content (MC) of dry maize seed.

| Moisture content (% $wb^A$) | Holding time (h) |
|---|---|
| From Initial MC to 16 | 16 |
| 16 to 21 | 1.5 |
| 21 to 24 | 0.25 |

$^A$wb = wet base

Fractions from sieves No. 5 through 12 were collected and aspirated to remove hulls using a Test Model Duo-aspirator (Carter Day International, Minneapolis, Minn.). The fraction retained by sieve No. 5 consisted mostly of whole or partially broken kernels. The majority of free embryos were retained by sieves No. 5 and 7. These two embryo fractions were treated at higher air velocity to aspirate the embryo-rich fraction away from heavier debris. The combined embryo-rich fractions accounted for 77% of the total embryo amount with purity of approximately 35%. To obtain high-purity embryos, the free embryos were handpicked. The moisture content of various fractions was determined by completely drying 2 to 5 grams of each sample at 125° C. for 6 hours, and calculating the loss in mass as percent moisture.

Effect of Protease Inhibitors on Avidin Stability

Dry maize kernels (12% MC; 500 g per batch) were first cracked using a roller mill (Ferrell-Ross, Oklahoma City, Okla.), then flaked to 0.3 mm thickness using Roskamp flaking rolls (Model K, Roskamp Mfg., Inc., Waterloo, Iowa.). The particle size distribution of flaked material was determined by sieving (see Table 1).

Twenty grams of flaked kernels were extracted with 200 ml of Tris-HCl pH 7.9 containing 500 mM NaCl, 1 mM $CaCl_2$ with stirring for 30 min at ambient temperature. One extraction was performed in the absence of protease inhibitors (control) and one in the presence of a protease inhibitor mixture containing 10 mM 2-mercaptoethanol (2-ME), 5 mM ethylenediamine tetraacetic acid (EDTA), 0.1 mM phenylmethanesulfonyl fluoride (PMSF), and 0.2 mM Diazo-N-acetyl-N-Leu-MeO. EDTA and 2-ME were added at the beginning of the extraction, and PMSF and diazo-N-acetyl-N-Leu-MeO were added 15 minutes after the extraction began. The insoluble residue was separated by centrifugation at 20,500×g for 25 minutes at 0° C. The supernatant was filtered through four layers of cheesecloth. The extracts were sampled at 0, 3, 6 and 22 hours for biotin binding activity [Durance T. D: Residual avidin activity in cooked egg white assayed with improved sensitivity. J. Food Sci. 56:707 (1991).and for protein integrity on western blots. For a positive control, chicken egg white avidin (Sigma Chemical Co.) was dissolved in the extraction buffer and samples were taken as above for activity assays.

Proteins from the above sampling times were separated by SDS-PAGE on 10% gels. Following electrophoresis, the gel was soaked for 10 min in 1× Bjerrum and Schafer-Nielsen transfer buffer [Durance, supra]. Proteins from the pre-soaked acylamide gel were transferred onto a 0.2 µm nitrocellulose membrane using a semidry-electroblotting apparatus (BioRad, Richmond, Calif.). The nitrocellulose membrane was incubated in 10% (w/v) dry milk in PDS-T at room temperature for 30 min followed by overnight incubation in anti-avidin antibody diluted 1:1000 in blocking buffer. Excess antibody was removed by washing the membrane 4× with PBS-T. The membrane was incubated with Protein-A gold (Bio-Rad) diluted 1:100 in blocking buffer until pink protein bands were visible.

Storage Stability

Seven 500 gram batches of maize kernels were cracked and flaked as described in the previous section. Flaked samples, 50 g each, were placed in zip-lock bags and stored at each of four different temperatures (−29, 10, 25 and 37° C.) up to 95 days. Avidin stability experiments were performed in triplicate; three 50 g samples per time and per temperature. To determine the activity of avidin, a 20 g sample was taken from each of the three 50 g bags at the specified time and extracted with 200 ml of the extraction buffer as described above.

Purification of Avidin from Maize

Thirty grams of transgenic maize seed were ground for 1 minutes in a coffee grinder. The meal was extracted for one hour at 4° C. with constant stirring at a 5:1 (w/v) ratio in a buffer containing 50 mM sodium carbonate (pH 11.0), 500 mM NaCl, 5 mM EDTA, and 0.05% Tween-20. The extraction mixture was centrifuged at 10,000 rpm for 15 minutes in a Sorvall GSA rotor at 4° C. The supernatants were removed and filtered through 4 layers of cheesecloth. The filtrate was centrifuged at 10,000 rpm for 15 minutes in a Sorvall SA 600 rotor at 4° C. The supernatant was recovered and the pH adjusted to 10.5, then centrifuged at 11,000 rpm for 30 minutes in an Eppendorf Type 16f6-38 rotor. The supernatant was incubated with 5 ml of 2-iminobiotin agarose [32] for 1 hour at 4° C. with constant agitation, the resin placed in a column and washed with 150 mL of a solution containing 50 mM sodium carbonate (pH 11.0), 2.0 M NaCl, 5 mM EDTA, and 0.05% Tween-20. The resin was washed again with the same buffer but without Tween-20. Avidin was eluted from the resin with 20 mM acetic acid. Each fraction (2 ml) was neutralized with 0.1 M NaOH. The fractions which contained avidin were dialyzed against $ddH_2O$ overnight.

Results.

Construction of Expression Cassettes Containing the Avidin and Bar Genes.

A gene optimized for expression of avidin protein in maize was generated by annealing and ligating overlapping, complementary synthetic oligonucleotide sequences that were based on codon usage bias for maize. Additionally, a DNA sequence encoding the barley alpha amylase signal sequence was generated via the same approach, and was ligated to the 5' terminus of the avidin gene in such a way that normal cellular processing of the translated pre-avidin protein would accurately cleave the signal sequence yielding mature avidin protein. This signal sequence was included based on the prediction that higher levels of avidin expression could be obtained if newly synthesized avidin protein was targeted to the extracellular compartment. The expression cassette (FIG. 1A) included in addition to the avidin segment, the maize ubiquitin promoter and the pinII terminator from potato. The ubiquitin promoter is considered a constitutive promoter that shows limited tissue specificity we have shown here that it drives high levels of expression particularly directed to the embryo.

The expression cassette for the selectable marker gene, phosphinothricin phosphotransferase (ppt), which encodes resistance to the herbicide bialaphos, [bar; 44; FIG. 1B], included the 35S promoter derived from Cauliflower Mosaic Virus sequences [Nagy F, Odell J T, Morelli G, Chua N H: Properties of expression of the 35S promoter from CaMV in transgenic tobacco plants. Biotechnology in plant science: relevance to agriculture in the eighties. Milton Zaitlin, Peter Day, and Alexander Hollaender, eds. Academic Press, Orlando, Fla. p. 227–235 (1985).] and the pinII terminator from potato. Expression cassettes similar to this have been shown to confer resistance to bialaphos in maize tissue culture.

Generation of Avidin-expressing, Transgenic Plants.

Regenerable embryogenic calli transformed by particle bombardment were selected on bialaphos for 10 weeks. Resistant calli were subjected to ELISA analysis to confirm the expression of the avidin gene. Plants initially regenerated from selected embryogenic tissue ($T_0$) were used as females in crosses with an untransformed inbred as the pollen donor. Regenerated $T_0$ plants were screened for high expression of avidin in leaf tissue (>0.1% of extracted protein). $T_1$ seed from an event showing high leaf expression, was screened to confirm high levels of expression in seed tissue as well. Avidin expression was segregating in the $T_1$ generation, and some seed was negative. However, expression in positive seeds ranged from 2.1–5.7% of aqueous extractable protein (determined by ELISA).

Characterization of the High-expressing Avidin Transformant.

Molecular Biology

Five individual $T_1$ plants from this event were analyzed for their DNA structure (FIG. 2). The linked avidin and bar genes were segregating as a single unit among individuals in these populations, and it was not surprising to find the genes present in only three plants. The avidin gene copy number was estimated at three to five as determined by DNA blot hybridization using an SphI digest of genomic DNA When double digests using SphI and SpeI were conducted to determine the size of the plant transcription unit, five separate fragments could be identified, none of which were the same size as the original plasmid-derived plant transcription unit—two were smaller and three were larger (FIG. 2A). Similarly, the selectable marker gene, bar, was present at four copies. In double digests probed with the bar gene (FIG. 2B), a band of the correct size was present, but these plants also contained two other transcription unit sizes, one smaller and one larger than the original construct. The avidin and bar inserts appear to be inherited as a single linkage unit, and it is not clear which of the inserts is active in transcription and translation. Similar integration patterns were present in all plants examined.

Cell Biology

Figure 3A:
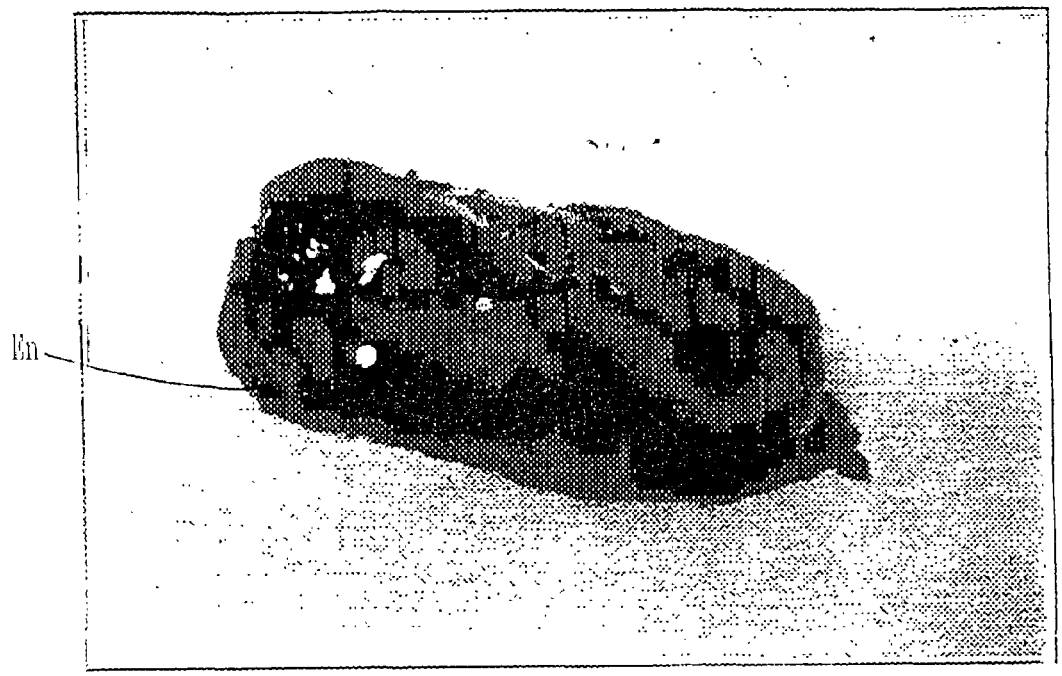
Figure 3B:
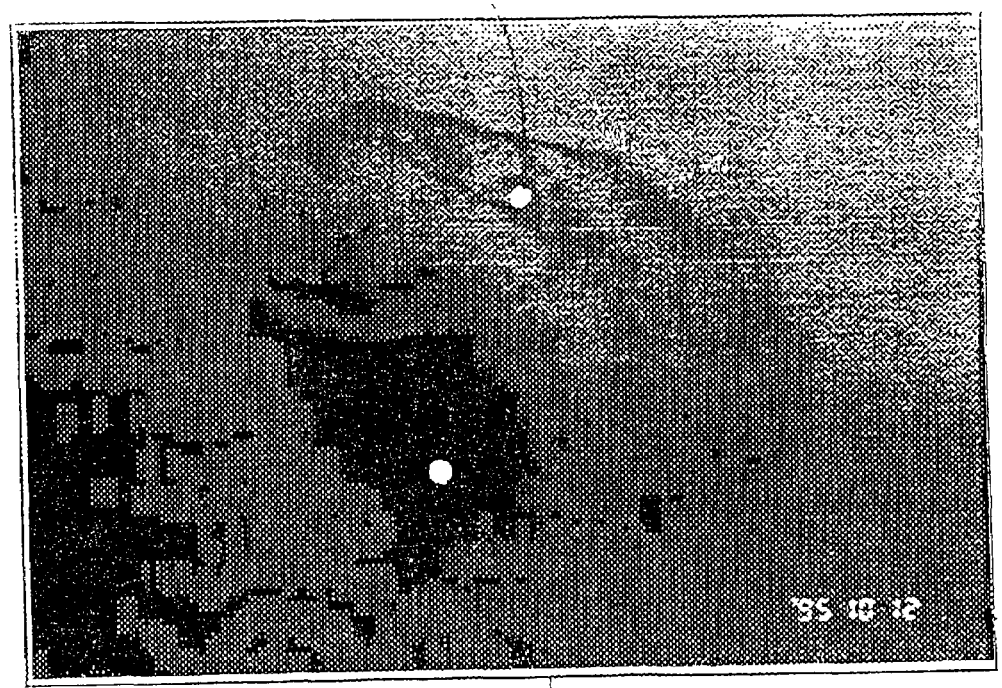
Figure 3C:
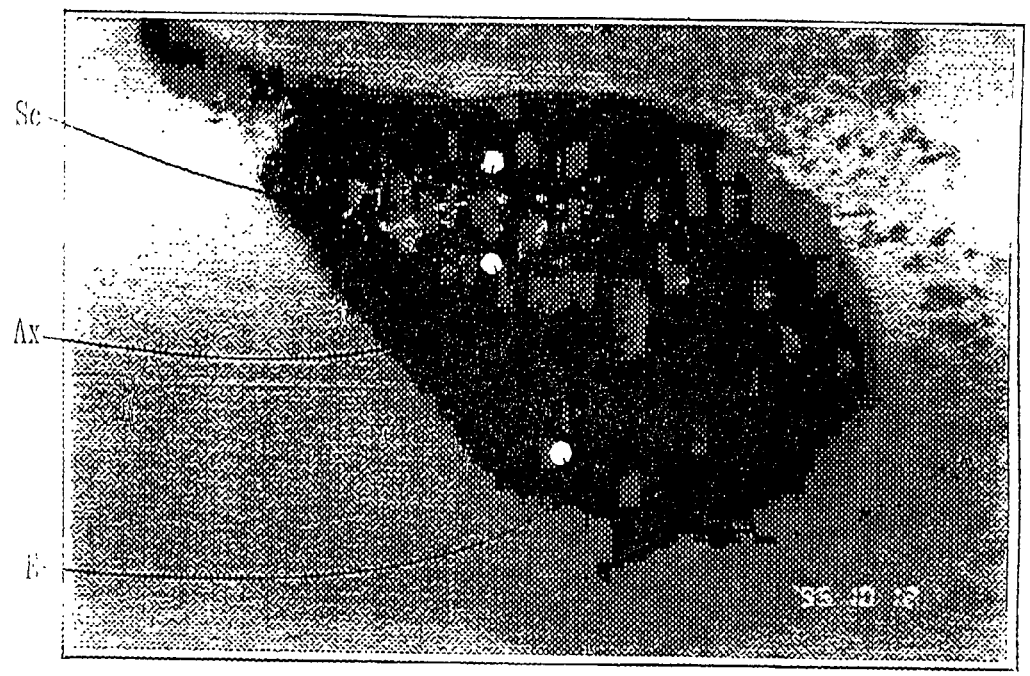
Figure 3D:
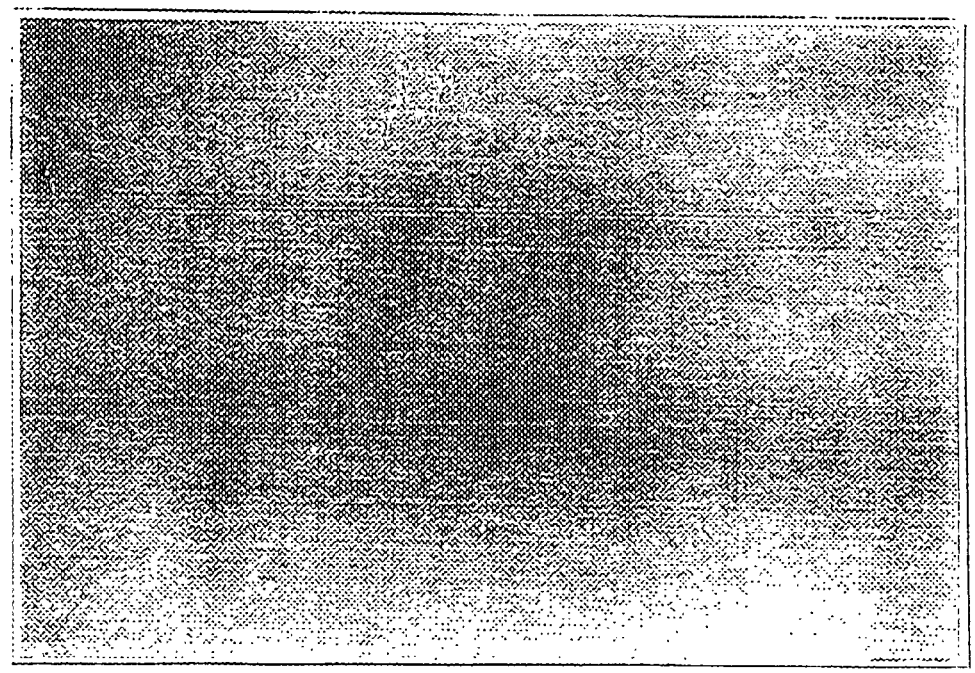

In seeds of the transgenic maize plants, avidin protein is primarily localized to the embryo. This was determined through tissue printing (FIG. 3) and embryo versus endosperm extraction and quantitation of avidin protein. Within the embryo, tissue prints reveal that the scutellum is the major sink of avidin, with the embryo axis accumulating somewhat lesser amounts (FIG. 3B, 3C). In extraction studies, the endosperm, which represents approximately 80% of the total kernel weight, contains just 22% of the avidin activity found in whole kernels. An additional 5% of the activity is present in the hulls (pericarp), also shown by tissue printing. The embryo, however, contains at least 55% of the avidin protein found in whole dry seed. The avidin protein balance indicates that 18% of the total activity is not accounted for and possibly is lost during dry milling.

Figure 4A:
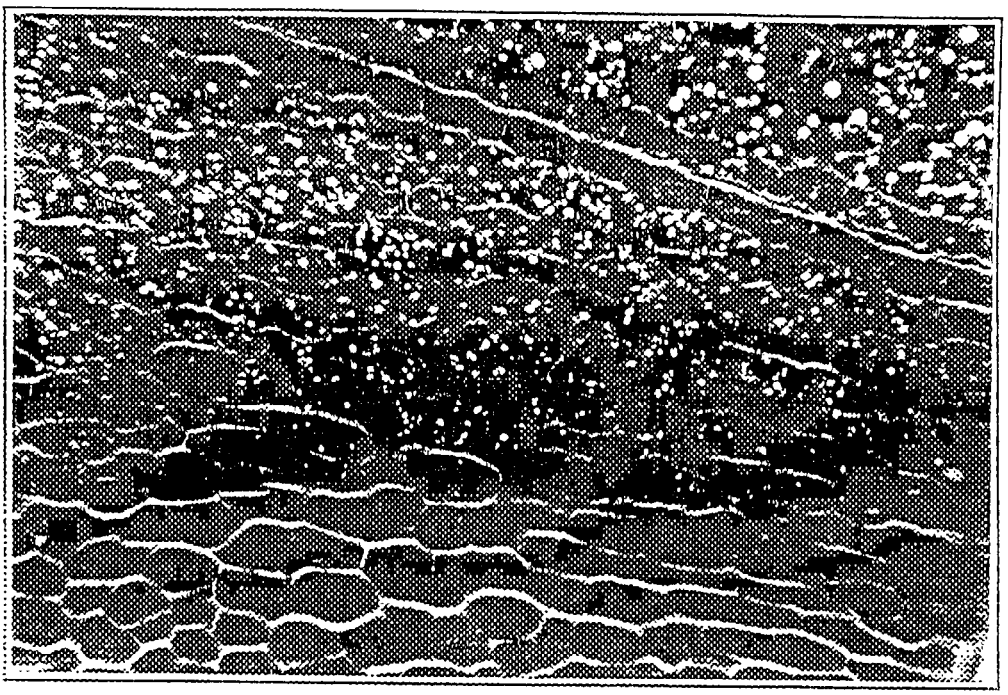
Figure 4B:
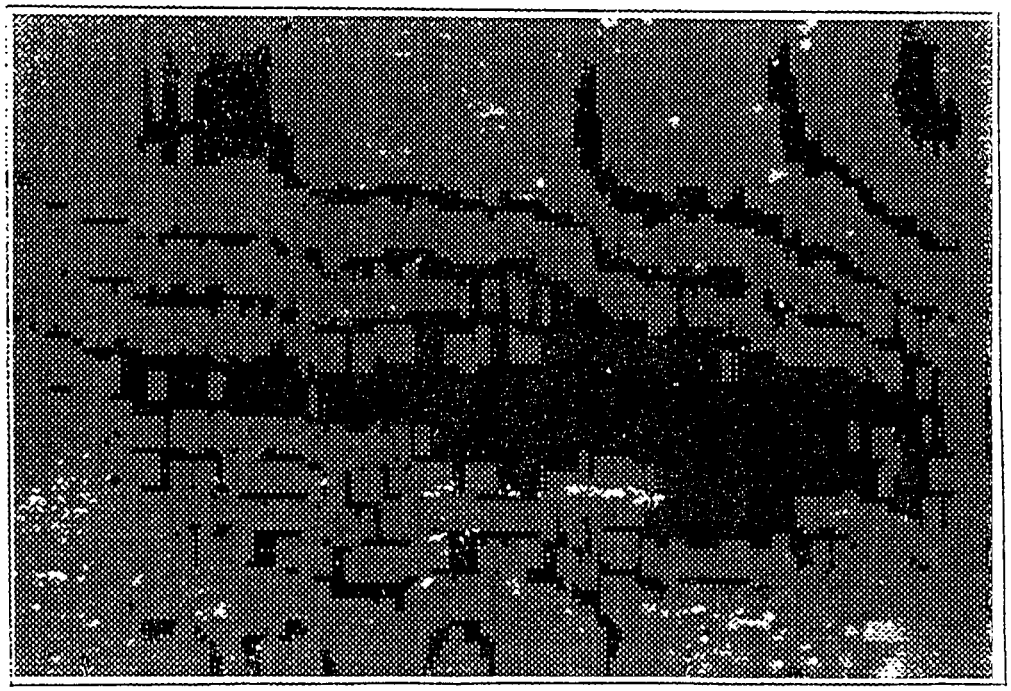

In situ localization experiments were performed on thin sections of embedded embryos using anti-avidin primary antibodies and TRITC fluorescent labeled secondary antibodies (FIG. 4). Phase contrast images of embedded sections showed excellent preservation of the cellular structure (FIG. 4A). Fluorescence was present in cell walls indicating that avidin is primarily localized to that organelle (FIG. 4B).

Genetics

Biolistic transformation of maize was performed using the Hi-II tissue culture line [Armstrong C L, Green C E, Phillips R L: Development and availability of germplasm with high Type II culture formation response. Maize Gen. Coop. Newsletter, 65:92–93 (1991). Bradford M: A rapid and sensitive method for the quantification of microgram quantities of protein utilizing the principle of protein-dye binding. Anal. Biochem. 72:248–254 (1976)]. This genotype is highly regenerable, flowers and usually sets seed in the greenhouse in the $T_0$ generation. However, because $T_0$ plants regenerated from tissue culture often exhibit problems with fertility and/or pollen transmission of the transgene, an outcross was performed in this first generation with pollen from an elite Pioneer inbred line, PHN46. The seed from this first outcross was planted in a winter nursery for seed increase.

This avidin-expressing line lost resistance in the $T_1$ generation to the herbicide on which it was originally selected in culture. Thus, a different scheme was required to identify transformed plants in the field in subsequent generations. Therefore, we pursued polymerase chain reaction (PCR) as an alternative method to select avidin-positive plants. Additionally, however, many of the plants exhibited male sterility, and a 97.5% correlation was observed between presence of the avidin gene (by PCR) and the male sterile/limited fertility phenotypes (Table 3). This same phenomenon also occurred in other avidin-positive lines, making it highly unlikely that the phenotype was a result of foreign gene insertion into a native gene required for pollen development The male sterile phenotype was subsequently used for scoring of transformed plants. PCR results indicated that 50–55% of plants in one field contained the avidin gene, the expected result from crossing a hemizygous female plant with a wild-type pollen donor.

TABLE 3

Correlation of male sterile/limited fertility phenotype with presence of the avidin gene as determined by PCR.

| PCR Result | # Fertile | # Partially Sterile | # Sterile |
| --- | --- | --- | --- |
| + | 1 | 6 | 32 |
| − | 40 | 0 | 1 |

Production

A program was designed to scale up the production of seed from this avidin-positive line, the goal of which was to obtain sufficient material from which to purify commercial quantities of recombinant avidin protein. It was critical to determine if the expression of avidin varied when the plants were grown in different locations or if expression was reduced in later generations because of gene inactivation.

Taking advantage of winter nurseries, we initiated a backcross program with this transgenic avidin-positive maize line to establish the transgene in two high quality elite Pioneer inbreds, that when crossed, will produce a high-yielding hybrid. The phenotype of $T_3$ generation plants was vigorous and seed yield was increased above the $T_1$ generation. The high levels of avidin protein in this transformed line were associated with male sterility, i.e., the anthers lacked pollen. Therefore, for seed production, vigorous inbred or hybrid lines and fertile sibling plants (Table 4) were used as pollen bearing parents. Ears were harvested only from plants showing loss of fertility, and the seed was shelled and bulked.

TABLE 4

Expression level of avidin protein as a percent of aqueous-extractable protein in T1 through T4 generations of maize seed.

| Location[A] | Avidin as % of extracted protein | Pollen parent | mg Avidin per kg seed |
| --- | --- | --- | --- |
| greenhouse | 0.8[B] (T1) | PHN46[G] | 80 |
| 1 | 3.0 ± 0.40[C] (T2) | PHN46 | 300 |
|  | 1.5 ± 0.16[D] (T3) | 3394 | 150 |
|  | 2.4 ± 0.10[E] (T4) | +sibs | 240 |
| 2 | 1.9 ± 0.23[D] (T3) | 3162 | 190 |
| 3 | 1.8 ± 0.19[D] (T3) | 3394 +sibs | 180 |
| 4 | 3.0 ± 0.11[F] (T3) | 3394 +sibs | 300 |
| average | 2.3% |  | 230 |

[A]Locations: 1. Hawaii winter nursery, Hawaii isolation field, (T3); Hawaii isolation field, (T4); 2. Texas winter nursery, (T3); 3. Johnston, IA isolation field, (T3); 4. Nebraska isolation field, (T3).
[B]Mean of 10 individuals.
[C]Mean of two bulk populations of 20 seeds each, three replicates each; ± standard error of the mean.
[D]Mean of six populations of 20 seeds and three bulk populations of 50 seeds each; ± standard error of the mean.
[E]Mean of two bulk populations of 10 seeds each; ± standard error of the mean.
[F]Mean of six bulk populations of 20 seeds each; ± standard error of the mean.
[G]PHN46, Pioneer elite inbred; Pioneer hyrdid; sibs, fertile siblings from previous out-cross.

The data show the levels of avidin present in extracts from seed produced in four different planting locations and over four generations ($T_1$–$T_4$). Quantitation of avidin levels in production seed lots was done by ELISA analysis. Because the avidin gene can only be inherited from the female and is hemizygous in those plants, the harvested seed contains a near 50:50 mixture of avidin positive and negative kernels and quantitative estimates incorporate both phenotypes. The expression of avidin was at a level that would yield an estimated 150–300 mg avidin per kg of harvested seed, the average being 230 mg per kg of seed. Because the pollen donors utilized to date are the same in locations where protein levels vary (compare locations 1, 3 and 4 in Table 4), they do not appear to be a factor in variation of protein yield in the seed. The various growing locations were chosen to test whether environmental conditions might affect protein accumulation in the seed. In this context, several observations were made. First, the gene encoding for avidin is not silenced in later generations (as demonstrated in expression at $T_3$ and $T_4$). Second, the variation in avidin as percent of extractable protein among locations was not attributable to any obvious genetic or environmental condition. The level of avidin expression is slightly lower in $T_3$ generation seed but this range of variation in $T_3$ seed is similar to that observed in seed from a single location (Hawaii) over several generations.

Because only 50% of the seed recovered from sterile plants carries the heterologous gene, the plants in subsequent production fields must be screened for phenotype, either using PCR or DNA isolated from leaf samples, or by scoring for male sterility. The avidin-expressing transgenic plants produced at least one ear with approximately 300–400 kernels, i.e., a 300–400-fold increase. Therefore, 1 kg of transgenic seed should yield approximately 150–200 kg, assuming 50% segregation in the seed source. We produced 160 kg of transgenic avidin seed from 1 kg of starting material, a 300-fold increase. This yield can be attributed to good growing conditions, high plant quality, efficiency in scoring male sterility and successful pollination.

Processing

Seed drying and processing as currently practiced require an elevated temperature which potentially could destroy avidin activity in the whole kernel as well as in the flaked material. Therefore, the effect of temperature on avidin activity was investigated. Avidin in whole kernels was stable and could withstand temperatures up to 50° C. for at least 7 days without loss of activity. This allows the seed to be dried using conventional practices which typically operate at temperatures of 41° C. for three days. In addition, our data (FIG. 5) indicate that avidin retains its original activity in the processed flaked material for up to 95 days at −29° C. and 10° C . Likewise, no significant change in avidin activity was measured when flakes were stored at 25° C. for up to 21 days. However, almost 50% of the initial avidin binding activity was lost when flaked material was stored at 37° C. for 7 days. The sample-to-sample variability (large standard deviation) was most likely caused by the variability in the activity assay when used on crude seed extracts. In any event, the thermostabilty of avidin in flakes and whole kernels allows significant flexibility in terms of storage, processing and transportation conditions to ensure integrity during delivery to the desired purification site.

Extraction and Purification

We have established that equal amounts of avidin protein can be extracted from seed subjected to either cracking and flaking, or to grinding into flour (data not shown). Therefore, the less labor-intensive flaking was selected as the method of choice for seed processing prior to the protein extraction step.

For commercial scale purification, avidin is extracted in a sodium bicarbonate/sodium chloride buffer (pH 11) containing Tween-20 and EDTA. The extract contains a complex mixture of proteins. as shown by Coomassie Blue staining of proteins electrophoretically separated in a 10% SDS-polyacrylamide gel (FIG. 6A lanes 2 and 3). Avidin is affinity purified from this complex mixture by incubating the extract with 2-iminobiotin agarose [Heney G, Orr G A: The purification of avidin and its derivatives on 2-iminobiotin-6-aminohexyl-sepharose 4B. Anal. Biochem. 114:92–96 (1981)]. The binding is efficient, as no avidin protein is detected by western blot analysis of the column void (FIG. 6B, void). As determined by ELISA and western blot analyses, avidin is quantitatively eluted from this column in two fractions. (FIGS. 6A and 6B).

The monomeric molecular weight of native avidin from chicken egg white is 17,600 Da [Gope et al., supra]. It is a glycoprotein with a single carbohydrate chain attached to the Asn-17 amino acid residue. In addition to the major glycosylated form of avidin, two minor molecular weight variants are visible on a stained gel or western blot when >2μg of purified maize-derived avidin are loaded per lane (FIGS. 6A and 6B). One minor variant has a molecular weight of 12,500 Da and comigrates with the deglycosylated form (see FIG. 9). A second minor variant has a molecular weight of approximately 9,000 Da. When sequencing was performed on this smallest variant, it was found that the N-terminal 42 amino acids of the mature protein including the glycosylation site were missing.

The source of the 9,000 Da fragment is not known, and we hypothesized that it could be due to a proteolysis occurring during initial grinding and extraction steps. If so, addition of protease inhibitors to the extraction buffer might reduce this minor proteolysis of avidin. However, activity assays show that at 22 hours after extraction, avidin activity is not significantly different in the presence or absence of protease inhibitors (Table 5).

TABLE 5

The effect of protease inhibitors on avidin stability

| Time (h) | Without inhibitors (μg ml$^{-1}$) | With inhibitors (μg ml$^{-1}$) | Control avidin (μg ml$^{-1}$) |
| --- | --- | --- | --- |
| 0 | 32.0 | 32.5 | 88.2 |
| 1 | 41.1 | 27.1 | 62.6 |
| 3 | 23.8 | 31.4 | 61.1 |
| 6 | 32.3 | 32.9 | 60.6 |
| 22 | 21.0 | 29.7 | 59.6 |

In addition, western blot analysis of these same fractions showed no degradation product that reacted with anti-avidin antibodies (FIG. 7), even when the gels were over-loaded. This indicates that extracted avidin is quite stable and the proteolytic fragment may be the result of a cellular event prior to seed grinding.

Physical Characterization of Avidin from Transgenic Maize Seed.

A comparison of the physical characters of the native and maize-derived avidin was performed and the amino-terminal sequence of the two proteins as determined by Edman degradation [Matsudaira P. J. Biol. Chem. 262:10035–10038 (1987)] was revealed to be identical (Table 5). Egg-white and maize-derived avidins were also compared on stained SDS-polyacrylamide gels and western blots (FIG. 6). The protein in maize seed extract and in purified form has a molecular weight of 16,800 Da (FIG. 6 lanes 1 and 2) based on migration of the standards in this gel system. This is approximately 800 Da smaller than the native chicken protein (FIG. 6 lanes 3 and 4). However, when proteins from both sources were digested with N-glycosidase A (NGA), the resulting deglycosylated forms were identical with a molecular weight of approximately 12,500 Da (FIG. 9). The smaller band in the lanes containing enzyme-treated samples is a protein from the enzyme preparation itself (compare lanes 3 and 5 to 6 in FIG. 9). These data combined with the N-terminal sequence data (Table 6) strongly suggest that the primary structure of the two avidins is identical.

TABLE 6

Summary of physical characterization data for native and maize-derived avidins.

| Avidin Source | N-Terminal Sequence | MW | glycosylation | Ki | antigenic similarity | pI |
|---|---|---|---|---|---|---|
| egg white | ARKCSLTGKWTNDLGSXMTI (SEQ ID NO:2) | 17.6 kDa | yes | 3.2 uM | identical | 10 |
| maize-derived | ARKCSLTGKWTNDLGSXMTI (SEQ ID NO:3) | 16.8 kDa | yes | 3.3 uM | identical | 10 |

In vivo, avidin exists as a homotetramer and its activity is to bind biotin to protect avian and reptilian eggs from pathogen invasion. Based upon this biotin-binding property, an analog of biotin, HABA, is utilized for the quantification of activity. Using the HABA binding assay, estimates of total avidin amounts in the fractions eluted from the affinity column were identical to estimates made by ELISA. When competitive binding studies were performed for avidin with biotin and HABA, the native and maize-derived avidins produced identical inhibition constants (Ki, Table 6). The deglycosylated form of chicken egg-white avidin binds biotin as well though it is not known if this is also true for the maize-derived recombinant avidin.

In additional experiments, other physical characteristics of the proteins were addressed (Table 6). Using ochterlony double diffusion, antigenic identity of native and recombinant avidins was confirmed (data not shown). The isoelectric point (pI) of the native and maize-derived avidins is at least 10, the highest (most basic) value for pI that can be experimentally determined (Table 6). This value correlates well with the calculated value of 10.4.

The localization of avidin to the cell wall matrix was not surprising as the gene was fused to a signal sequence, which targeted the protein to the endoplasmic reticulum during translation. In plants, the default pathway for proteins transported through the endoplasmic reticulum is secretion, because a protein's ultimate subcellular location depends on factors other than just the presence of the signal sequence, including topological information on the protein itself. For example, specific N- or C-terminal peptides direct vacuolar proteins to receptors that target them to the vacuole. When these sequences are removed, the proteins are secreted. These topological signals were not engineered onto the avidin gene construct and in this case, the protein was secreted.

EXAMPLE 2

Commercial Production of β-Glucuronidase

The protein β-Glucuronidase (GUS) has been produced in plants. See U.S. Pat. No. 5,804,694. Here, it is demonstrated that by using the germ of the seed in the plant in which the protein is produced, increased concentration of the protein on a dry weight basis is obtained.

Materials and Methods

Production of Transgenic Corn

The transgenic corn kernels were provided by Pioneer Hi-Bred International (Johnston, I A). The transgenic corn producing rGUS was prepared by using transformation, selection, and plant regeneration methods reported by Hood, E. E., et al., (1997) Commercial production of avidin from transgenic maize: Characterization of transformant, production, processing, extraction and purification. Molecular Breeding 3:291–306.

Degermination

The germ was separated from the endosperm by a dry-milling process (Pen J, Sijmons P C, van Ooijen A J J, Hoekema A: Protein production in transgenic crops: Analysis of plant molecular farming. Industrial Crops Production. Elsevier, Amsterdam. pp. 241–250 (1993B)). Five hundred grams of dry corn kernels (12% moisture) were placed in a polyethylene bag and moisture conditioned at 4° C. to the preselected moisture content (MC) by adding water according to the schedule shown in Table 7.

TABLE 7

Conditioning schedule for germ separation from corn kernels

| Moisture content (% wet basis) | Holding time (h) |
|---|---|
| IM to 16 | 16 |
| 16 to 21 | 1.5 |
| 21 to 24 | 0.25 |

IM—initial moisture (12–14%)

After conditioning the kernels were passed through a horizontal custom-made dehuller/degermer operated at 16,000 rpm with a feed rate of approximately 300 g/min. The dehulled and degermed kernels were air-dried at ambient temperature to around 15% moisture and fractionated through a series of sieves (No. 3.5, 5, 7, 12, 25, and 50 Standard testing Sieves, Fisher Scientific, Philadelphia, Pa.). The fractions retained by sieves No. 3.5 through 12 were collected and aspirated to remove the hulls using a Test Model Duo-aspirator (Carter Day International, Minneapolis, Minn.). The fraction retained by sieve No. 3.5 consisted mostly of whole or partially broken kernels. The majority of the germ was retained by sieves No. 5 and 7. The germ fractions from sieves No. 5 and 7 were aspirated at higher air velocity to obtain a germ-rich fraction. The combined germ-rich fractions contained 77% of the initial germ amount.

Distribution of rGUS in the Corn Kernel Tissue Corn kernels (100 g) were soaked in deionized water for two days. In two days separation of germ, hull and endosperm was completed and soaked for 2–3 days. The first half was soaked for 2 days, and the other half for 3 days. The hulls, endosperm, and germ were manually separated. Each fraction was air-dried at ambient temperature and ground with a coffee grinder (Salton/Maxim Housewares Inc., Mont. Prospect, Ill.). rGUS activity and the moisture content of each ground sample were determined. rGUS activity was determined using the assay described by Jefferson and Wilson (Jefferson, R. A.; Wilson, K. J. (1991). In The GUS Gene Fusion system. In "Plant Molecular Biology Manual", Vol. 1, B14, (S. B. Gelven, R. A. Schilperoort and D. P. S. Verma, eds.). Kluwer Academic Publisher, Dordrecht, Belgium. pp.1–33). One unit (U) of rGUS activity was defined as the amount of enzyme that converts one nmole of p-nitrophenyl β-D-glucuronide per minute at pH 7.0 and 37° C.

Storage and Heat Stability

Dry corn kernels (12% moisture, 500 g per batch) were cracked using a roller mill (Ferrel-Ross, Oklahoma City, Okla.), then flaked to 0.3 mm thickness using Roskamp flaking rolls (Model K, Roskamp Mfg., Inc., Waterloo, Iowa.). Seven 500-gram batches of flaked corn kernels were placed in zip-lock bags and stored at each of four different temperatures for up to 95 days. The storage stability study was performed in triplicate; three 50-g samples per time and per temperature. To determine the activity of GUS, a 20-g sample was taken from each of the three 50-g bags at the specified time and extracted with 200 ml of 20 mM Tris-HCl pH 7.9 containing 500 mM NaCl and 1 mM $CaCl_2$. Extraction was carried out using a paddle mixer at ambient temperature for 30 min.

The heat stability of rGUS at temperature above 50° C. was studied by heating corn kernels in a convection oven Isotemp 500 series (Fisher, Pittsburgh, Pa.). Ten-gram batches of corn kernels were placed in separate aluminum pans and placed in the oven at four different temperatures (50, 70, 90 and 125° C.) for up to eight hours. The heat stability study was performed in duplicate; two 10-g samples per time and per temperature. Heat-treated corn kernels were ground using a coffee grinder prior to extraction. Three-gram ground samples were extracted with 30 ml of 50 mM NaPi pH 7.5 and GUS activity in the extract was determined.

rGUS Extraction

A portion of the germ sample prepared by the degermination process was defatted by using a Soxhlet apparatus. Forty grams of full-fat germ were extracted with 300 ml of hexane for five hours, and then air-dried at ambient temperature to remove the hexane.

All samples (flaked kernels, full-fat germ and defatted germ) were ground using a coffee grinder before protein extraction. The samples were extracted at 1:4 or 1:10 solid-to-liquid ratio with 50 mM NaPi buffer of pH 7.5. The extraction was carried out for 15 minutes at ambient temperature by using a magnetic stirrer for mixing less than 50-ml and a paddle mixer for greater than 50-ml volumes. After stirring, the suspension was centrifuged at 26,000 g for 25 min at 0° C., and then filtered through a 4-layer of cheesecloth. The extract was assayed for GUS activity (Hood et al., supra) and protein (Jefferson, R. A.; Wilson, K. J. (1991). In The GUS Gene Fusion system. In "Plant Molecular Biology Manual", Vol. 1, B14, (S. B. Gelven, R. A. Schilperoort and D. P. S. Verma, eds.). Kluwer Academic Publisher, Dordrecht, Belgium. pp.1–33).

The efficiency of rGUS extraction was qualitatively examined by staining the spent solids with 0.1% X-Gluc (5-bromo-4-chloro-3-indolyl-β-D-glucupyranoside) solution. After the extraction, spent solids were separated by centrifugation at 26,000 g, rinsed extensively with water to remove the remaining rGUS, and dried at ambient temperature. To a 100 mg of washed and dried solids, 2 ml of 0.1% x-Gluc solution were added and the suspension was incubated at 37° C. for 30 minutes. The presence of a blue precipitate (stain) in the solids indicated incomplete extraction of rGUS.

The extraction yield was estimated by SDS-PAGE followed by a Western blot analysis. A 500-μl aliquot of the 2× SDS-PAGE sample buffer was added to 100 mg of washed and dried solids. The mixture was boiled for 5 minutes, and 15-μl aliquots were loaded on the gel. SDS-PAGE was carried out on a 10% resolving gels at a constant voltage of 150 V (Bradford, M. A rapid and Sensitive Method for the Quantitation of Microgram Quantities of Protein Utilizing the Principle of Protein-dye Binding. Anal. Biochem. 1976, 72, 248–254). Following the SDS-PAGE, the gel was soaked for 10 min in Bjerrum and Schafer-Nielsen transfer buffer (39). Protein bands from the presoaked acrylamide gel were transferred onto a 0.2-μm nitrocellulose membrane at a constant voltage of 10 V for 30 min using a semidry-electroblotting apparatus (BioRad, Richmond, Calif.). The nitrocellulose membrane was incubated in a blocking solution containing 10% milk diluent solution (Kirkegaard and Perry, Gaithersburg, Md.) in PBS-T at ambient temperature for 30 min followed by an overnight incubation with polyclonal anti-GUS in the blocking solution. The excess antibody was removed by washing the membrane with PBS-T. The membrane was then incubated with Protein-A gold solution (Bio-Rad, Hercules, Calif.). The immunoreactive protein bands were enhanced by silver staining (Bio-Rad, Hercules, Calif.) and quantified by densitometry.

Purification Recombinant GUS was purified from ground kernels, full-fat germ and defatted germ using a three-step chromatography. Ground corn kernels (75 g), full-fat germ (7.5 g), and defatted germ (7.5 g) samples were extracted with 50 mM NaPi buffer pH 7.5 (buffer A) at 1:4 or 1:10 solid-to-liquid ratio as described in the previous section. Fifteen ml of DEAE-Toyopearl (Supelco, Bellefonte, Pa.) resin in buffer A were added to the centrifuged and filtered extract to adsorb (capture) rGUS. The slurry was mixed with a magnetic stirrer for 15 min at ambient temperature, filtered through a funnel-supported No. 1 filter paper, and washed with 400 ml of buffer A. The washed DEAE resin was packed into a glass column with an inside diameter of 1.5 cm. The adsorbed rGUS was eluted with 0.3 M NaCl in buffer A. The fractions containing rGUS activity were combined, ammoniumsufate (AS) was added to a final concentration of 1 M, and the solution was filtered through a 0.45 μfilter. The filtered solution was applied to a 12 ml of octyl-Sepharose column (Pharmacia, Piscataway, N.J.) pre-equilibrated with buffer A containing 0.3 M NaCl and 1 M ammonium sulfate (buffer B). The column was first washed with 15–20 column volumes (CV) of buffer B followed by buffer A (9–13 CV) containing 150 mM NaCl and 500 mM AS to elute the loosely bound protein. rGUS was eluted by applying 200 ml of NaCl/AS (105 mM/350 mM to 52 mM/175 mM) gradient in Buffer A. The flow rate during sample loading, washing, and elution was maintained at 2 ml/min. The fractions containing GUS activity were combined and diafiltered against distilled water using a Centriprep-30 concentration unit (Amicon, Beverly, Mass.). The diafiltered sample was applied to a second DEAE-Toyopearl column pre-equilibrated with Buffer A. After loading the sample, the column was washed with 3 CV of the same buffer, and rGUS was eluted with 200 ml of 0 to 0.3 M NaCl gradient in Buffer A. The purity of rGUS was estimated by densitometry of protein bands on the SDS-PAGE gel (38), which was stained with Coomassie blue.

Results and Discussion

Storage and Heat Stability

The handling of harvested corn includes drying the kernels to a final moisture content below 15% and storing the corn at different temperatures depending on the required length of storage, relative humidity of air, the kernel moisture content, and the end application. Drying, storage, and processing (milling) temperatures of transgenic corn is of a particular importance because integrity and activity of the recombinant protein must be preserved. For example, during drying as well as in the commercial corn milling kernels could be exposed to temperatures as high as 100° C. At the end, the primary (upstream) processing of transgenic corn (milling, degermination, fractionation, oil extraction, etc.) will probably be performed at a site different than the bioprocessing (downstream processing) plant, and processed corn may require different temperature regime for transporting and storing than that established for commercial grain. For these reasons, we have investigated the storage and heat stability of rGUS in processed corn (flaked kernels) and whole kernels, respectively.

Storage stability study (FIG. 10) showed that no significant loss of rGUS activity occurred when flaked kernels were stored at −29, 10, or 25° C. for up to 2 weeks. When flaked kernels were stored at 37° C. for one week, 23% of the initial rGUS activity was lost. Storing the flaked kernels at −29 and 10° C. for up to 3 months resulted in 14% and 23% loss of rGUS activity, respectively. At ambient temperature (25° C.), a sample spoilage was observed after three weeks and a loss of 13% of the initial GUS activity was measured. Therefore, flaked kernels can be transported and stored at ambient temperature (25° C.) for a period of less than two weeks without affecting rGUS activity. If necessary, flaked kernels can be stored for up to two months at 10° C. A similar storage stability data were obtained for recombinant avidin in transgenic corn Pen et al, supra.

The heating of whole kernels with initial MC of 12.6% at 50° C. for up to eight hours did not affect rGUS activity (FIG. 11). The prolonged heat stability study indicated that rGUS activity in the kernels was fully retained for up to six days at 50° C. (data not shown). Heating at 70° C. for one hour also did not significantly affect rGUS activity, but after 8 hours 60% of its initial activity was lost. No residual rGUS activity was observed after heating the kernels for one hour at 90° C. and for 10 minutes at 125° C.

The heat stability results obtained in the laboratory were validated on a large scale. During the processing of 1,000 kg of transgenic corn in a custom-milling plant located in Grinnell, Iowa, the corn was exposed for a short time (less than 1 min) to 90° C. The milled corn was bagged at approximately 50° C., transported at ambient temperature (30° C.) for two hours to Iowa State University, and then stored overnight at 10° C. before the rGUS activity was determined. Sampling of milled transgenic corn revealed no loss of rGUS activity, which indicated that lab-scale heat-stability data could be used to predict the effect of the storage and processing temperature on the recombinant protein.

Extraction of rGUS

To determine the effect of extraction parameters on rGUS activity, eight process variables were screened using a quarter factorial design experiment. Based on the analysis of screening experiments, the following extraction conditions were used in the subsequent studies: 1) 50 mM NaPi buffer of pH 7.5; 2) minimum of 1:4 solids-to-buffer ratio; and 3) mixing for at least 15 minutes at ambient temperature. The screening experiments revealed that particle size distribution of the ground corn (i.e. flaked vs. milled corn) and the mixing speed did not significantly affect the extraction yield. In addition, the presence of 0.5 M NaCl, 0.05% (v/v) of Tween-20 and a cocktail of protease inhibitors consisting of 10 mM ME, 5 mM ethylenediamine tetraacetic acid (EDTA), 1 mM phenylmethyl sulphonyl fluoride (PMSF), 0.2 M dioazoacetyl D,L-norleucine methyl ester (diazo AcNleOMe) in the extraction buffer did not increase the recovery of rGUS activity.

To determine whether a complete extraction of rGUS from corn kernels, full-fat germ and defatted germ was achieved, the remaining solids were stained with X-Gluc. The visual examination of the spent solids revealed the presence of blue stained particles indicating an incomplete extraction of rGUS from ground corn kernels, full-fat germ, and defatted germ. The Western blot analysis of the spent solids confirmed the presence of unextracted rGUS. We estimated that about 70% of rGUS was extracted from the ground kernels with the phosphate or borate buffer alone (FIG. 12, lanes 2 and 4). Changing the pH of the extraction buffer to pH 10 did not affect the extraction efficiency. When 1% (v/v) of SDS and 2% (v/v) of ME were included in the extraction buffer rGUS was completely extracted (FIG. 12, lane 3), but the enzyme was inactive. The subsequent dialysis of SDS did not yield active protein. Interestingly, a complete extraction of rGUS could not be achieved when either SDS or ME was missing in the extraction buffer suggesting a synergistic action of these two components.

Further attempts to increase the extraction yield by adding 1% (v/v) of either Triton X-100 or Tween-20 to the extraction buffer did not show any yield improvement. Because in general, the primary product recovery is critical for effective downstream processing, an additional research effort to maximize the extraction yield of rGUS will be needed.

Distribution of rGUS in the Kernel

The fractionation of the transgenic kernels into hulls, endosperm, and germ tissue, showed that approximately 93% of the total rGUS activity was located in the germ and the remaining 7% in the endosperm (Table 8).

TABLE 8

Distribution of rGUS in the corn kernel

|  | Germ | Endosperm |
| --- | --- | --- |
| Amount of tissue (%) | 13 | 80 |
| rGUS activity (U/g tissue) | 6800 | 80 |
| rGUS activity (%) | 93 | 7 |

The staining of the kernel cross-sectional area with X-Gluc solution confirmed that majority of rGUS activity was produced in the germ tissue. Neither the extraction nor the tissue staining showed any rGUS accumulation in the hulls. Because the germ usually accounts for 10–13% of the dry kernel weight and contains 93% of rGUS activity, the separation of the germ tissue before the protein extraction step could considerably reduce the cost of downstream processing by reducing the amount of total solids in the process and by increasing the concentration of rGUS in the extract. For example, the concentration of the rGUS (μg/mg of soluble protein) in the germ extract was twice as high as that in the whole kernel extract (Table 9).

Effect of the Starting Material on the Extraction and Purification of rGUS

Because the distribution study showed that more than 90% of rGUS is located in the germ, we have separated the germ by a dry-milling process. The degermination of transgenic corn kernels performed in our laboratory resulted in a germ-rich fraction of 50% purity; the balance consisted of endosperm and hulls. After extracting the corn oil from part of the germ-rich fraction, the three different starting materials (ground kernels, full-fat germ, and defatted germ) containing rGUS activity were extracted and compared (Table 9). The ground kernel, full-fat germ, and defatted germ fractions contained 3.3, 20.0, and 2.0% (w/w) corn oil, respectively (Table 9). The rGUS concentration (µg/ml) in the germ extract was six-to ten times greater than that in kernel extract at either 1:4 or 1:10 solid-to-liquid. Because total corn protein concentration was also greater in the germ than in the kernel extract, the concentration of rGUS was approximately 0.4% and 0.2% of the total soluble protein in the germ and the kernel extract, respectively. For all three starting materials, 30% more rGUS and soluble protein per gram of dry solids were extracted at 1:10 than at 1:4 solid-to-liquid ratio. The amounts of rGUS extracted from the full-fat germ and defatted germ at either 1:4 or 1:10 solid-to-liquid ratio were similar indicating that 1) the corn oil extraction with hexane (~60° C.) did not affect the activity of rGUS, and 2) the high-oil content (20%) in the initial material did not interfere with the protein extraction. The stability of rGUS during hexane extraction is an important finding which shows that, prior to the protein extraction, the corn oil could be recovered and sold as a co-product. When full-fat germ is considered as a starting material for recovery of recombinant proteins, 1:10 solid-to-liquid ratio is recommended because at 1:4 ratio the extract was rather viscous. Although not observed on a lab-scale, the increased extract viscosity could be a problem in the scaled-up capture chromatography step. The purification data summarized in Table 10 indicate that rGUS can be purified with a similar effectiveness from either extract. Apparently, neither starch in the kernel extract nor the oil presence in full-fat germ extract affected the purification yield and the final purity (specific activity) of rGUS, which was estimated at 50%. To determine whether and how much the extract impurities would foul the DEAE resin after repeated use, we have performed ten on-and-off capture chromatography cycles using the full-fat germ extract (1:10 ratio). No change in the resin capacity and rGUS yield was observed after ten cycles. The rGUS concentration factor achieved after the capture chromatography step was fifteen fold for the kernel extract and five fold for the germ extracts, whereas the purification factor for all three extracts was about five fold.

TABLE 9

Extraction of rGUS from ground corn kernels, full-fat germ, defatted germ[a]

| Sample | Corn kernels | Full-fat germ | De-fatted germ | Corn kernels | Full-fat germ | De-fatted germ |
|---|---|---|---|---|---|---|
| Solid-to-liquid ratio | 1:4 | 1:4 | 1:4 | 1:10 | 1:10 | 1:10 |
| Initial oil content (%, db) | 3.3 | 20.0 | 2.0 | 3.3 | 20.0 | 2.0 |
| rGUS (µg/ml) | 5 | 35 | 60 | 2 | 16 | 23 |

TABLE 9-continued

Extraction of rGUS from ground corn kernels, full-fat germ, defatted germ[a]

| Sample | Corn kernels | Full-fat germ | De-fatted germ | Corn kernels | Full-fat germ | De-fatted germ |
|---|---|---|---|---|---|---|
| rGUS (µg/g dry solids) | 17 | 170 | 180 | 23 | 220 | 220 |
| rGUS (µg/mg soluble protein) | 1.9 | 3.4 | 3.9 | 1.8 | 3.6 | 3.5 |
| Total protein (mg/g dry solids) | 9.3 | 50 | 47 | 13 | 61 | 61 |

[a] All values are average of two replications with less then 10% deviation

EXAMPLE 3

Cost Comparisons Using Germ

The following demonstrates the cost savings that is expected in using the germ portion of the seed for protein expression, extraction and purification, versus using the entire seed. Table 10 demonstrates production of a protein useful in pharmaceutical applications will result in production costs expected to be $1/10^{th}$ the cost of using the seed. In this projection, protein production is expected to be higher, since the starting material will contain a higher concentration of protein per kilogram of material versus the seed. Thus, more protein will be produced from a smaller amount of material. At 80% purification yield shown, there is a more than six times cost difference. In fact, purification yields using germ are expected to reach 85%, which would resulted in an eight times greater cost savings in using germ. Table 11 shows details of costs to produce defatted germ containing the protein.

Yet another comparison, using rGUS purification from flaked corn, full fat germ and defatted germ further demonstrates the higher yield, better purification and high quantities of rGUS per sample, summarized at Table 12. Tables 13 and 14 compare costs of extracting rGUS from full-fat corn germ and flaked corn, respectively. As can be seen there is considerable savings in using germ.

TABLE 10

Projected Cost Comparison of Protein Production Using Germ vs. Seed

| Large Scale Protein Production from Germ in Corn | Large scale Protein Production in Corn |
|---|---|
| Assumptions: Starting material: 45,500 kg/batch flaked germ Defatted germ cost $2.80/kg (cost of corn + dry milling + oil extraction)-see Table 11 below Recombinant protein concentration: 1 wt % of germ 45,00 kg germ contains 4500 kg of extractable corn protein and 450 kg of extractable rec. | Assumptions: Starting material: 45,500 kg/batch flaked corn Flaked corn cost: $0.16/kg (cost of corn + milling) Rec. protein concentration: 0.1 wt % of seed 45,500 kg flaked corn will contain 430 kg extractable corn protein and 45 kg of extractable |

TABLE 10-continued

Projected Cost Comparison of Protein Production Using Germ vs. Seed

| Large Scale Protein Production from Germ in Corn | | Large scale Protein Production in Corn | |
|---|---|---|---|
| protein | | rec. protein | |
| 10 workers/shift operating in 3 shifts | | 10 workers/shift operating in 3 shifts | |
| Final protein product will contain 20 wt % recombinant protein | | Final protein product will contain 20 wt. % recombinant protein | |
| Purification yield-80% | | Purification yield-80% | |
| Credits: | | Credits: | |
| grits @$0.33/kg | | hominy feed @ $0.10/kg | |
| crude oil @$0.52/kg | | | |
| hominy fee @ $0.10/kg | | | |
| Simulation Results: | | Simulation Results: | |
| Total Equipment cost: | $ 3,800,000 | Total Equipment Cost: | $ 3,520,000 |
| Direct Fixed Capital: | $24,000,000 | Direct Fixed Capital: | $22,000,000 |
| Total Annual Operating Cost: | $70,000,000 | Total Annual Operating Cost: | $16,600,000 |
| Total Credits: | $46,000,000 | Credits: | $ 1,600,000 |
| Grits Credits | $41,000,000 | | |
| Crude oil | $ 1,800,000 | | |
| Feed | $ 3,200,000 | | |
| Rec. Protein (kg/yr) | 150,000 | Protein Product (kg/yr): | 15,000 |
| Rec. Protein Production Cost ($/kg): | $    160 | Rec. Production Cost ($/kg): | $    1,130 |

TABLE 11

Cost to Produce Defatted Germ Containing HSA

| | Amount (kg) | Total Cost ($) | Unit Cost ($kg) | Comments |
|---|---|---|---|---|
| Raw Material | | | | |
| Transgenic Corn Processing | 45,000 | 7,200 | 0.16 | $0.16/kg |
| Dry-milling | 45,000 | 1,800 | 0.04 | $0.04/kg ($1/bu) |
| Germ-oil extraction | 3,150 | 126 | 0.04 | 10% germ, 70% germ yield: Extr. Cost = $0.04/kg germ flakes |
| Total Cost | | 9,126 | | |
| Co-Product Credits | | | | |
| Grits | 22,500 | 7425 | 0.33 | Assume 50% of total corn |
| Crude oil | 598.5 | 311.22 | 0.52 | 20% oil content |
| Hulls + tip caps (7% of corn) | 3,150 | 693 | | |
| Hominy feed (Hulls + tip caps + germ) | 6,300 | | 0.11 | |
| Total Credits | | 8429 | | |
| NET PRODUCTION COST of 1 kg germ | 3150 | 697 | 0.22 | |
| Unit Cost of HSA before recovery and purification | 31.5 | | 22 | HSA content 0.1 wt % of corn or 1 wt % of germ |

TABLE 14

Comparison of rGUS purification from different samples

| Sample | Flaked corn | Full-fat germ | Defatted germ |
|---|---|---|---|
| Solid-to-liquid ratio | 1:4 | 1:10 | 1:10 |
| Yield (%) | 36 | 44 | 47 |
| Purification fold | 300 | 350 | 330 |
| Specification activity *U/mg) | 36,000 | 45,000 | 36,000 |
| Purified rGUS per g sample (mg/g) | 0.006 | 0.040 | 0.056 |

TABLE 13

Cost of Extracting rGUS from Full-fat Corn Germ

| Processing Cost | $/day | $/kg corn | $/lb corn | $/bu corn |
|---|---|---|---|---|
| Germ separation | 681.75 | 0.150 | 0.068 | 3.82 |
| Extraction | 54.70 | 0.012 | 0.005 | 11.20 |
| Drying | 14.61 | 0.003 | 0.001 | 0.08 |
| TOTAL | 751.06 | 0.165 | 0.075 | 15.10 |
| Cost of Materials | | | | |
| Corn | 2,000 | 0.440 | 0.200 | 11.20 |
| Water | 0.21 | 0.000 | 0.000 | 0.00 |
| Na2HPO4 | 34.11 | 0.008 | 0.003 | 0.19 |
| NaH2PO4 | 4.41 | 0.001 | 0.000 | 0.02 |
| TOTAL | 2,038.74 | 0.449 | 0.204 | 11.42 |
| Co-product Credits | | | | |
| Dry spent solids | 474.64 | 0.104 | 0.005 | 0.27 |
| TOTAL | 474.64 | 0.104 | 0.005 | 0.27 |
| TOTAL COST | 2,315.15 | 0.509 | 0.274 | 26.25 |
| rGUS in extract (kg) | 0.067 | 0.134 | 0.201 | |
| Cost/kg rGUS | $34,523 | $17,261 | $11,508 | |

TABLE 14

Cost of Extracting rGUS from Flaked Corn

| Processing Cost | $/day | $/kg corn | $/lb corn | $/bu corn |
|---|---|---|---|---|
| Milling | 92.71 | 0.020 | 0.009 | 0.52 |
| Extraction | 710.23 | 0.156 | 0.071 | 3.98 |
| Drying | 340.13 | 0.075 | 0.034 | 1.90 |
| TOTAL | 1,143.07 | 0.251 | 0.114 | 6.40 |
| Cost of Materials | | | | |
| Corn | 2,000 | 0.440 | 0.200 | 11.20 |
| Water | 2.73 | 0.001 | 0.000 | 0.02 |
| Na2HPO4 | 443.06 | 0.097 | 0.044 | 2.48 |
| NaH2PO4 | 57.33 | 0.013 | 0.006 | 0.32 |
| TOTAL | 2,503.11 | 0.551 | 0.250 | 14.02 |
| Co-product Credits | | | | |
| Dry spent solids | 441.52 | 0.097 | 0.044 | 2.47 |
| TOTAL | 441.52 | 0.097 | 0.044 | 2.47 |
| TOTAL COST | 3,204.66 | 0.705 | 0.320 | 17.95 |
| rGUS in extract (kg) | 0.089 | 0.177 | 0.266 | |
| Cost/kg extractable GUS | $36,209.14 | $18,104.57 | $12,069.71 | |

EXAMPLE 4

Laccase Produced in Plant Germ

Isolation and Cloning of Laccase Encoding DNA

The gene for laccase was cloned from *Trametes versicolor* by the methods described here, with isolated RNA reverse transcribed into cDNA. The sequence is set forth in FIG. 13A–C.

Preparation of Plasmids

The plasmids containing the barley alpha amylase signal sequences were produced by ligating oligomeric sequences encoding the sequence to the 5' end of the laccase gene, then the entire sequence amplified by PCR and cloned into a vector.

The sequencing of individual clones followed and confirmed the presence of the construct. An individual clone was chosen for further manipulations. To generate plasmid 7718 (FIG. 14) intermediate vectors with BAASS:: laccase were cut with NcoI and HpaI and ligated into vector 2774, which contains the ubiquitin promoter and PinII terminator. The entire transcription unit was cut from 2774 with NheI and NotI and ligated to 3770 containing the 35S promoter with the PAT selectable marker between the left and right borders of the *Agrobacterium tumefaciens* gene. For plasmid pPGN8908 (FIG. 15) the same procedure was employed, and the ubiquitin promoter of the 2774 vector removed, substituting the globulin promoter. The globulin promoter in p3303 was cut with HindIII and NcoI, and vector 2774 having the ubiquitin, barley alpha amylase, laccase and PinII sequences was cut with the same restriction enzymes. The two pieces were then ligated to create plasmid KB254. While there are several approaches possible for preparing the plasmid, in this procedure the HindIII and NarI site from KB254 was used to cut p7718 and substitute the globulin promoter for the ubiquitin promoter in 7718.

Transformation of Maize

Fresh immature zygotic embryos were harvested from Hi-II maize kernels at 1–2 mm in length. The general methods of *Agrobacterium* transformation were used as described by Japan Tobacco, at Ishida, Y, H Saito, S Ohta, Y Hiei, T Komari and T Kumashiro. 1996. "High efficiency transformation of maize (*Zea mays* L.) mediated by *Agrobacterium tumefaciens*" *Nature Biotechnology* 14:745–750 with the modifications described supra. Fresh embryos were treated with 0.5 ml log phase *Agrobacterium* strains EHA 101. Bacteria were grown overnight in a rich medium with kanamycin and spectinomycin to an optical density of 0.5 at 600 nm, pelleted, then re-inoculated in a fresh 10 ml culture. The bacteria were allowed to grow into log phase and were harvested at no more dense than OD600=0.5. The bacterial culture is resuspended in a co-culture medium. For transient expression assays, embryos (5–10 per tube) were sonicated in the presence of the bacteria for 30 sec (Trick H and J Finer. 1997. "SAAT: sonication-assisted *Agrobacterium*-mediated transformation." *Transgenic Research* 6-.329–336), then plated on a solid medium as above. Embryos and bacteria were co-cultivated for 5 days.

For stable transformations, embryos not subjected to sonication were transferred to a bialaphos selective agent on embryogenic callus medium and transferred thereafter every two weeks to allow growth of transformed type II callus. Plants were regenerated from the callus.

Detection of Expression of Laccase

The corn tissue was analyzed by a laccase activity assay and stable expression of laccase confirmed. Expression levels are shown in Table 15 as percent total soluble protein

TABLE 15

| Plasmid | Expression in T1 seed |
|---------|----------------------|
| p7718   | 0.08                 |
| p8908   | 0.14                 |

The laccase activity assay uses one of the mediators, ABTS (2,2-azino-bis-(3-ethylbenzthiazoline-6-sulfonic acid)) and can use a smaller or larger sample which increases the detectable amounts 100×. In this procedure, 0.2 ml of ABTS was introduced into a cuvette and 1.5 ml of NaOAc at a pH of 5.0 added. One blanks the cuvette, then 0.1 ml of the enzyme sample is added and mixed. Using a spectrophotometer, the change of absorption was measured at 420 nm, every 24 hours for 4 days. One ABTS unit is defined as a change of A420 per minute/2 provided the sample is not diluted. This assay can also be done in a microtiter plate format.

Southern analysis is a well known technique to those skilled in the art. This common procedure involves isolating the plant DNA, cutting with restriction endonucleases and fractionating the cut DNA on an agarose gel to separate the DNA by molecular weight and transferring to nylon membranes. It is then hybridized with the probe fragment which was radioactively labeled with $^{32}P$ and washed in an SDS solution. Southern, E., "Detection of a specific sequences among DNA fragments by gel electrophoresis" *J. Mol. Biol.* 98:503–517 (1975). Northern analysis is also a commonly used technique by those skilled in the art and is similar to Southern analysis except that RNA is isolated and placed on an agarose gel. The RNA is then hybridized with a labeled probe. Potter, E. et al. "Thyrotropin releasing hormone exerts rapid nuclear effects to increase production of the primary prolactin mRNA transcript" *Proc. Nat. Acad. Sci. U.S.A.* 78:6662–6666 (1981). A Western analysis is a variation of this technique, where instead of isolating DNA, the protein of interest is isolated and placed on an acrylamide gel. The protein is then blotted onto a membrane and contacted with a labeling substance. See e.g., Hood et al. "Commercial Production of Avidin from Transgenic Maize; Characterization of Transformants, Production, Processing, Extraction and Purification" *Molecular Breeding* 3:291–306 (1997).

Expression levels of laccase that are produced that are commercially attractive are as follows. While levels at about 0.01% are commercially useful, expression levels of 0.1% total soluble protein would be even more attractive, as it would allow recovery of 100 mg protein from 22 pounds of corn, which would cost approximately $1.20 to $2.00 for the processed corn. These figures become more commercially viable as expression levels increase. At levels of 1.0%, 100 mg of protein could be recovered from 2.2 pounds of corn at a cost of about $0.10 to 0.20 for the processed corn, and with levels of 10%, 100 mg of protein could be recovered from 0.22 pounds of corn at a cost of about $0.01–0.02 for the processed corn.

Attempts to Extract Laccase from Plants $T_0$ plants were generated as described above, using the p8098 vector to introduce laccase expressing nucleotide sequences into plants. Seed from a number of highly expressing lines were taken to the field for analysis in subsequent backcross generations. Expression is stable over several generations with the highest expression in a pooled sample reaching greater than 50 ppm seed weight. Defatted laccase germ flour was sequentially extracted with SAT containing 0.5 M NaCl. It was found that even after the extracts no longer showed significant laccase activity (less than 1% of the total), the cell debris that remained was positive for laccase activity using DAF (2,7 diaminofluorene) at the same intensity as non-extracted defatted laccase germ flour. This indicated that not all of the laccase was extractable under aqueous conditions although the laccase remaining in the seed was active. Extraction with a number of different buffers including detergents, salts, various pHs and protease inhibitors did not result in any additional laccase activity being extracted (data not shown). Grinding the defatted laccase germ flour to an approximately 10-fold smaller particle size than coffee grinder-ground germ allowed the extraction of approximately twice as much active laccase (600 ng laccase/mg germ flour vs. 280 ng laccase/mg germ flour). Thus at least some laccase is physically trapped in the cell wall matrix.

Use of Laccase Germ in Bio-glue Applications

The gelling ability of recombinant laccase extracted and concentrated from maize was compared to a concentrated fungal broth from *Aspergillus* containing recombinant *Trametes* laccase. A dilution series of equal amounts of laccase (as measured by extracted activity) was added to lignin sulfonate and incubated at room temperature with constant mixing for 4 hours before the viscosity of the solutions was evaluated qualitatively. The procedures used were as follows. Two grams of CBOS-4 Marasperse lignin sulfonate (Lignotech, USA) were dissolved in 10 ml citrate/phosphate buffer (50 mM citric acid, 100 mM $Na_2PO_4$) and adjusted to pH 5–5.5 with citric acid. Laccase preparations were incubated with 0.9 ml of lignin sulfonate solution in 1.3×10 cm borosilicate glass tubes at room temperature with constant end-over-end rotation at ~12 rpm (adapted from method in patent application WO 00/34402). After a four hour incubation, samples were rated qualitatively for viscosity on a scale of 0 (no change in viscosity) to 3 (completely solid). Laccase defatted corn germ was pre-treated 1:3 w/v with 20 mM sodium acetate, before addition to the lignin sulfonate preparation, to avoid solidification due to absorption of the buffer from the lignin sulfonate preparation.

Only the highest amount (160 μg) of fungal laccase caused a change in viscosity. In contrast, a similar change in viscosity occurred with only 80 μg of maize-produced laccase concentrate, with complete gelling seen when 160 μg of maize-produced laccase concentrate was used (FIG. 16). However, the best results were obtained by using defatted corn germ flour containing laccase directly in the gelling experiment. Corn germ containing laccase expressing at approximately 140 ng/mg defatted germ (as measured by extractable activity) was incubated with the lignin sulfonate. The sample that contained only 7 μg of laccase (as measured by extractable activity) gelled the lignin sulfonate as well as 80 μg of maize-produced laccase concentrate or 160 μg of fungal-produced laccase concentrate, and 14 μg of extractable laccase in corn germ caused complete solidification of the sample (FIG. 16). A representative bench-scale test using both concentrated laccase corn extract and laccase defatted corn germ directly are shown (FIG. 17). In the tubes containing the laccase, the lignin sulfonate has become extremely viscous, coating the interior surfaces of the tube as it was rotated, whereas the lignin sulfonate in the control tubes is still very fluid. The dark pieces on the sides of the control corn germ tube are pieces of corn germ that did not slide to the bottom. Therefore, laccase may be extracted from plants and used in commercial processes, but use of laccase in plant germ provides considerably better performance.

Thus it can be seen the invention accomplishes at least all of its objectives.

What is claimed is:

1. A method of commercial production of heterologous laccase in plant tissue comprising:
   (a) transforming monocotyledonous plant tissue with a construct comprising a globulin or a ubiquitin plant-compatible promoter operably linked to a nucleic acid encoding laccase;
   (b) culturing a plant from the plant tissue;
   (c) growing the plant such that it produces seed, wherein the seed has germ;
   (d) harvesting the seed; and
   (e) separating the germ from the seed in a commercial milling process,
   wherein the germ has an increased concentration of laccase on a dry weight basis compared to the seed.

2. The method of claim 1, wherein the monocotyledonous plant tissue is selected from the group consisting of corn, sorghum, oats, barley or wheat plant tissue.

3. A method of decreasing the amount of plant tissue necessary to supply commercial quantities of heterologous laccase produced in a plant, wherein the method comprises
   transforming monocotyledonous plant tissue with a construct comprising a globulin or a ubiquitin plant-compatible promoter operably linked to a nucleic acid encoding laccase;
   growing the plant tissue such that it produces a plant producing seed, wherein the seed has germ;
   separating the germ of the seeds, and
   supplying the germ as a source of commercial quantities of laccase,
   wherein the laccase is expressed in the germ.

4. The method of claim 3, wherein the monocotyledonous plant tissue is selected from the group consisting of corn, sorghum, oats, barley or wheat plant tissue.

5. A method of supplying heterologous laccase produced in plants in an industrial use, wherein the method comprises:
   transforming monocotyledonous plant tissue with a construct comprising a globulin or a ubiquitin plant-compatible promoter operably linked to a nucleic acid encoding laccase;
   growing the plant tissue such that it produces a plant producing seed, wherein the seed has germ;
   separating the germ tissue from the seed; and
   supplying the germ tissue as the source of laccase for an industrial use,
   wherein the laccase is expressed in the germ.

6. The method of claim 5, wherein the industrial use is the production of fiberboard.

7. The method of claim 5, wherein the industrial use comprises degradation of lignin-containing waste material.

8. The method of claim 5, wherein the industrial use comprises the polymerization of lignin-containing compounds.

9. The method of claim 5, wherein the industrial use comprises polymerization of lignin sulfonate.

10. The method of claim 5, wherein the industrial use comprises pulp bleaching.

11. The method of claim 5, wherein the monocotyledonous plant tissue is selected from the group consisting of corn, sorghum, oats, barley or wheat plant tissue.

12. A method of supplying heterologous laccase expressed in plants for commercial applications, wherein the method comprises:
   transforming monocotyledonous plant with a construct comprising a globulin or a ubiquitin plant-compatible promoter operably linked to a nucleic acid encoding laccase;
   growing the plant such that it produces seed, wherein the seed has germ;
   separating the germ tissue from the seed; and supplying the germ tissue as the source of laccase in commercial applications, wherein the laccase is expressed in the germ.

13. The method of claim 12, wherein the monocotyledonous plant tissue is selected from the group consisting of corn, sorghum, oats, barley or wheat plant tissue.

14. A method of improving recovery of costs of production of heterologous laccase in plants comprising transforming monocotyledonous plant tissue with a construct comprising a globulin or a ubiquitin plant-compatible promoter operably linked to a nucleic acid encoding laccase;

growing the plant such that it produces seed, wherein the seed has germ;

separating the germ from the seed;

supplying the germ as the source of laccase in a commercial application; and supplying the remaining tissue of the seed to a second commercial application, wherein the laccase is expressed in the germ.

15. The method according to claim 1, 3, 5, 12 or 14, wherein the promoter is a globulin promoter.

16. The method according to claim 1, 3, 5, 12 or 14, wherein the promoter is an ubiquitin promoter.

17. The method of claim 14, wherein the monocotyledonous plant tissue is selected from corn, sorghum, oats, barley or wheat plant tissue.

18. A monocotyledonous plant germ tissue separated from plant seed, comprising a heterologous nucleotide sequence encoding a laccase operably linked to a globulin or a ubiquitin plant-compatible promoter and having an increased concentration of the laccase on a dry weight basis compared to the seed.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      localization sequence

<400> SEQUENCE: 1

Lys Asp Glu Leu
  1

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      N-terminal egg white sequence
<220> FEATURE:
<221> NAME/KEY: MOD_RES
<222> LOCATION: (17)
<223> OTHER INFORMATION: Variable amino acid
```

-continued

```
<400> SEQUENCE: 2

Ala Arg Lys Cys Ser Leu Thr Gly Lys Trp Thr Asn Asp Leu Gly Ser
 1               5                  10                  15

Xaa Met Thr Ile
             20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      N-terminal maize-derived sequence
<220> FEATURE:
<221> NAME/KEY: MOD_RES
<222> LOCATION: (17)
<223> OTHER INFORMATION: Variable amino acid

<400> SEQUENCE: 3

Ala Arg Lys Cys Ser Leu Thr Gly Lys Trp Thr Asn Asp Leu Gly Ser
 1               5                  10                  15

Xaa Met Thr Ile
             20

<210> SEQ ID NO 4
<211> LENGTH: 1500
<212> TYPE: DNA
<213> ORGANISM: Trametes versicolor
<220> FEATURE:
<221> NAME/KEY: CDS
<222> LOCATION: (1)..(1497)

<400> SEQUENCE: 4
```

| | | | | | | | | | | | | | | | | |
|---|---|---|---|---|---|---|---|---|---|---|---|---|---|---|---|---|
| gcc | atc | ggg | ccg | gtg | gcg | agc | ctc | gtc | gtc | gcg | aac | gcc | ccc | gtc | tcg | 48 |
| Ala | Ile | Gly | Pro | Val | Ala | Ser | Leu | Val | Val | Ala | Asn | Ala | Pro | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | gac | ggc | ttc | ctt | cgg | gat | gcc | atc | gtg | gtc | aac | ggc | gtg | gtc | cct | 96 |
| Pro | Asp | Gly | Phe | Leu | Arg | Asp | Ala | Ile | Val | Val | Asn | Gly | Val | Val | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | ccg | ctc | atc | acc | ggg | aag | aag | gga | gac | cgc | ttc | cag | ctc | aac | gtc | 144 |
| Ser | Pro | Leu | Ile | Thr | Gly | Lys | Lys | Gly | Asp | Arg | Phe | Gln | Leu | Asn | Val | |
| | 35 | | | | | 40 | | | | | 45 | | | | | |

| | | | | | | | | | | | | | | | | |
|---|---|---|---|---|---|---|---|---|---|---|---|---|---|---|---|---|
| gtc | gac | acc | ttg | acc | aac | cac | agc | atg | ctc | aag | tcc | act | agt | atc | cac | 192 |
| Val | Asp | Thr | Leu | Thr | Asn | His | Ser | Met | Leu | Lys | Ser | Thr | Ser | Ile | His | |
| 50 | | | | | 55 | | | | | 60 | | | | | | |

| | | | | | | | | | | | | | | | | |
|---|---|---|---|---|---|---|---|---|---|---|---|---|---|---|---|---|
| tgg | cac | ggc | ttc | ttc | cag | gca | ggc | acc | aac | tgg | gca | gac | gga | ccc | gcg | 240 |
| Trp | His | Gly | Phe | Phe | Gln | Ala | Gly | Thr | Asn | Trp | Ala | Asp | Gly | Pro | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | gtc | aac | cag | tgc | cct | att | gct | tcc | ggg | cat | tca | ttt | ctg | tac | gac | 288 |
| Phe | Val | Asn | Gln | Cys | Pro | Ile | Ala | Ser | Gly | His | Ser | Phe | Leu | Tyr | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| ttc | cat | gtg | ccc | gac | cag | gca | gga | acg | ttc | tgg | tac | cac | agt | cat | ctg | 336 |
| Phe | His | Val | Pro | Asp | Gln | Ala | Gly | Thr | Phe | Trp | Tyr | His | Ser | His | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| tct | acg | caa | tac | tgt | gac | ggg | ctg | cga | gga | ccg | ttc | gtc | gtg | tac | gac | 384 |
| Ser | Thr | Gln | Tyr | Cys | Asp | Gly | Leu | Arg | Gly | Pro | Phe | Val | Val | Tyr | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | aag | gat | ccg | cac | gcc | agc | cgc | tac | gat | gtt | gac | aac | gag | agc | acg | 432 |
| Pro | Lys | Asp | Pro | His | Ala | Ser | Arg | Tyr | Asp | Val | Asp | Asn | Glu | Ser | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | atc | acg | ttg | acc | gac | tgg | tac | cac | acc | gct | gcc | cgg | ctc | ggt | ccc | 480 |
| Val | Ile | Thr | Leu | Thr | Asp | Trp | Tyr | His | Thr | Ala | Ala | Arg | Leu | Gly | Pro | |
| 145 | | | | | 150 | | | | | 155 | | | | | 160 | |

```
agg ttc cca ctc ggc gcg gac gcc acg ctc atc aat ggt ctt ggg cgg       528
Arg Phe Pro Leu Gly Ala Asp Ala Thr Leu Ile Asn Gly Leu Gly Arg
            165                 170                 175 tcg gcc tcc act ccc acc gcc gcg ctt gct gtg atc aac gtc cag cac       576
Ser Ala Ser Thr Pro Thr Ala Ala Leu Ala Val Ile Asn Val Gln His
        180                 185                 190 gga aag cgc tac cgc ttc cgt ctc gtt tcg atc tcg tgc gac ccg aac       624
Gly Lys Arg Tyr Arg Phe Arg Leu Val Ser Ile Ser Cys Asp Pro Asn
            195                 200                 205 tac acg ttc agc atc gac ggg cac aat ctg acc gtc atc gag gtc gac       672
Tyr Thr Phe Ser Ile Asp Gly His Asn Leu Thr Val Ile Glu Val Asp
210                 215                 220 ggt atc aac agc cag cct ctc ctt gtc gac tct atc cag atc ttc gcc       720
Gly Ile Asn Ser Gln Pro Leu Leu Val Asp Ser Ile Gln Ile Phe Ala
225                 230                 235                 240 gcg cag cgc tac tcc ttt gtg ttg aat gcg aac caa acg gtc ggc aac       768
Ala Gln Arg Tyr Ser Phe Val Leu Asn Ala Asn Gln Thr Val Gly Asn
            245                 250                 255 tac tgg gtc cgc gcg aac ccg aac ttc gga acg gtt ggg ttc gcc ggg       816
Tyr Trp Val Arg Ala Asn Pro Asn Phe Gly Thr Val Gly Phe Ala Gly
            260                 265                 270 ggg atc aac tcc gcc atc ctg cgc tac caa ggc gca cca gtc gcc gag       864
Gly Ile Asn Ser Ala Ile Leu Arg Tyr Gln Gly Ala Pro Val Ala Glu
            275                 280                 285 ccc act acg acc cag acg acg tcg gtg atc ccg ctt atc gag acg aac       912
Pro Thr Thr Thr Gln Thr Thr Ser Val Ile Pro Leu Ile Glu Thr Asn
        290                 295                 300 ttg cac ccc ctc gct cgc atg cct gtg cct ggc agc ccg aca ccc ggg       960
Leu His Pro Leu Ala Arg Met Pro Val Pro Gly Ser Pro Thr Pro Gly
305                 310                 315                 320 ggc gtc gac aag gcg ctc aac ctc gcg ttt aac ttc aac ggc acc aac      1008
Gly Val Asp Lys Ala Leu Asn Leu Ala Phe Asn Phe Asn Gly Thr Asn
            325                 330                 335 ttc ttc atc aac aac gcg act ttc acg ccg ccg acc gtc ccg gta ctc      1056
Phe Phe Ile Asn Asn Ala Thr Phe Thr Pro Pro Thr Val Pro Val Leu
            340                 345                 350 ctc cag att ctg agc ggt gcg cag acc gca caa gac ctg ctc cct gca      1104
Leu Gln Ile Leu Ser Gly Ala Gln Thr Ala Gln Asp Leu Leu Pro Ala
            355                 360                 365 ggc tct gtc tac ccg ctc ccg gcc cac tcc acc atc gag atc acg ctg      1152
Gly Ser Val Tyr Pro Leu Pro Ala His Ser Thr Ile Glu Ile Thr Leu
370                 375                 380 ccc gcg acc gcc ttg gcc ccg ggt gca ccg cac ccc ttc cac ctg cac      1200
Pro Ala Thr Ala Leu Ala Pro Gly Ala Pro His Pro Phe His Leu His
385                 390                 395                 400 ggt cac gcc ttc gcg gtc gtt cgc agc gcg ggg agc acc acg tat aac      1248
Gly His Ala Phe Ala Val Val Arg Ser Ala Gly Ser Thr Thr Tyr Asn
            405                 410                 415 tac aac gac ccg atc ttc cgc gac gtc gtg agc acg ggc acg ccc gcc      1296
Tyr Asn Asp Pro Ile Phe Arg Asp Val Val Ser Thr Gly Thr Pro Ala
            420                 425                 430 gcg ggc gac aac gtc acg atc cgc ttc cag acg gac aac ccc ggg ccg      1344
Ala Gly Asp Asn Val Thr Ile Arg Phe Gln Thr Asp Asn Pro Gly Pro
            435                 440                 445 tgg ttc ctc cac tgc cac atc gac ttc cac ctc gac gcg ggc ttc gcg      1392
Trp Phe Leu His Cys His Ile Asp Phe His Leu Asp Ala Gly Phe Ala
450                 455                 460 atc gtg ttc gca gag gac gtt gcg gac gtg aag gcg gcg aac ccg gtt      1440
Ile Val Phe Ala Glu Asp Val Ala Asp Val Lys Ala Ala Asn Pro Val
```

-continued

```
                    465                 470                 475                 480
ccg aag gcg tgg tcg gac ctg tgc ccg atc tac gac ggg ctg agc gag      1488
Pro Lys Ala Trp Ser Asp Leu Cys Pro Ile Tyr Asp Gly Leu Ser Glu
                485                 490                 495 gct aac cag tga                                                       1500
Ala Asn Gln <210> SEQ ID NO 5
<211> LENGTH: 499
<212> TYPE: PRT
<213> ORGANISM: Trametes versicolor

<400> SEQUENCE: 5

Ala Ile Gly Pro Val Ala Ser Leu Val Val Ala Asn Ala Pro Val Ser
  1               5                  10                  15

Pro Asp Gly Phe Leu Arg Asp Ala Ile Val Asn Gly Val Val Pro
                 20                  25                  30

Ser Pro Leu Ile Thr Gly Lys Lys Gly Asp Arg Phe Gln Leu Asn Val
             35                  40                  45

Val Asp Thr Leu Thr Asn His Ser Met Leu Lys Ser Thr Ser Ile His
 50                  55                  60

Trp His Gly Phe Phe Gln Ala Gly Thr Asn Trp Ala Asp Gly Pro Ala
 65                  70                  75                  80

Phe Val Asn Gln Cys Pro Ile Ala Ser Gly His Ser Phe Leu Tyr Asp
                 85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
130                 135                 140

Val Ile Thr Leu Thr Asp Trp Tyr His Thr Ala Ala Arg Leu Gly Pro
145                 150                 155                 160

Arg Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
        195                 200                 205

Tyr Thr Phe Ser Ile Asp Gly His Asn Leu Thr Val Ile Glu Val Asp
    210                 215                 220

Gly Ile Asn Ser Gln Pro Leu Leu Val Asp Ser Ile Gln Ile Phe Ala
225                 230                 235                 240

Ala Gln Arg Tyr Ser Phe Val Leu Asn Ala Asn Gln Thr Val Gly Asn
                245                 250                 255

Tyr Trp Val Arg Ala Asn Pro Asn Phe Gly Thr Val Gly Phe Ala Gly
            260                 265                 270

Gly Ile Asn Ser Ala Ile Leu Arg Tyr Gln Gly Ala Pro Val Ala Glu
        275                 280                 285

Pro Thr Thr Thr Gln Thr Thr Ser Val Ile Pro Leu Ile Glu Thr Asn
    290                 295                 300

Leu His Pro Leu Ala Arg Met Pro Val Pro Gly Ser Pro Thr Pro Gly
305                 310                 315                 320

Gly Val Asp Lys Ala Leu Asn Leu Ala Phe Asn Phe Asn Gly Thr Asn
                325                 330                 335
```

```
Phe Phe Ile Asn Asn Ala Thr Phe Thr Pro Pro Thr Val Pro Val Leu
            340             345             350

Leu Gln Ile Leu Ser Gly Ala Gln Thr Ala Gln Asp Leu Leu Pro Ala
        355             360             365

Gly Ser Val Tyr Pro Leu Pro Ala His Ser Thr Ile Glu Ile Thr Leu
    370             375             380

Pro Ala Thr Ala Leu Ala Pro Gly Ala Pro His Pro Phe His Leu His
385             390             395             400

Gly His Ala Phe Ala Val Val Arg Ser Ala Gly Ser Thr Thr Tyr Asn
            405             410             415

Tyr Asn Asp Pro Ile Phe Arg Asp Val Val Ser Thr Gly Thr Pro Ala
            420             425             430

Ala Gly Asp Asn Val Thr Ile Arg Phe Gln Thr Asp Asn Pro Gly Pro
            435             440             445

Trp Phe Leu His Cys His Ile Asp Phe His Leu Asp Ala Gly Phe Ala
            450             455             460

Ile Val Phe Ala Glu Asp Val Ala Asp Val Lys Ala Ala Asn Pro Val
465             470             475             480

Pro Lys Ala Trp Ser Asp Leu Cys Pro Ile Tyr Asp Gly Leu Ser Glu
            485             490             495

Ala Asn Gln
```